(12) United States Patent
Berg et al.

(10) Patent No.: US 7,595,321 B2
(45) Date of Patent: Sep. 29, 2009

(54) COMPOUNDS HAVING SELECTIVE INHIBITING EFFECT AT GSK3

(75) Inventors: Stefan Berg, Sodertalje (SE); Sven Hellberg, Sodertalje (SE)

(73) Assignee: AstraZeneca AB, Sodertalje (SE)

( * ) Notice: Subject to any disclaimer, the term of this patent is extended or adjusted under 35 U.S.C. 154(b) by 480 days.

(21) Appl. No.: 10/539,545

(22) PCT Filed: Dec. 15, 2003

(86) PCT No.: PCT/SE03/01957

§ 371 (c)(1),
(2), (4) Date: Jun. 16, 2005

(87) PCT Pub. No.: WO2004/055009

PCT Pub. Date: Jul. 1, 2004

(65) Prior Publication Data

US 2006/0116385 A1   Jun. 1, 2006

(30) Foreign Application Priority Data

Dec. 17, 2002   (SE) .................................. 0203753

(51) Int. Cl.
| | |
|---|---|
| A61K 31/4965 | (2006.01) |
| A61K 31/44 | (2006.01) |
| C07D 401/00 | (2006.01) |
| C07D 403/00 | (2006.01) |
| C07D 405/00 | (2006.01) |
| C07D 409/00 | (2006.01) |
| C07D 411/00 | (2006.01) |
| C07D 413/00 | (2006.01) |
| C07D 417/00 | (2006.01) |
| C07D 419/00 | (2006.01) |
| C07D 241/02 | (2006.01) |
| C07D 421/00 | (2006.01) |
| C07D 213/72 | (2006.01) |

(52) U.S. Cl. ............................. 514/255.05; 514/255.06; 514/340; 514/352; 544/405; 544/406; 546/268.1; 546/304

(58) Field of Classification Search .................. None
See application file for complete search history.

(56) References Cited

U.S. PATENT DOCUMENTS

| 5,472,823 A | 12/1995 | Hagiwara et al. |
| 6,255,307 B1 | 7/2001 | Cox et al. |
| 2001/0031772 A1 | 10/2001 | Schoenafinger et al. |
| 2006/0116385 A1 | 6/2006 | Berg et al. |
| 2006/0173014 A1 | 8/2006 | Berg et al. |

FOREIGN PATENT DOCUMENTS

| WO | WO 0160806 A2 | 8/2001 |
| WO | WO 0168612 A2 | 9/2001 |
| WO | WO 02092585 | 11/2002 |
| WO | WO 03093297 A2 | 11/2003 |
| WO | WO2003093297 | * 11/2003 |

OTHER PUBLICATIONS

Dorwald F. A. Side Reactions in Organic Synthesis, 2005, Wiley: VCH, Weinheim p. IX of Preface.*
Vippagunta et. al. Advanced Drug Delivery Reviews 48 (2001) 3-26.*
Office Action dated Sep. 4, 2008 for U.S. Appl. No. 10/539,543.
Office Action dated Sep. 15, 2008 for U.S. Appl. No. 10/539,546.
International Search Report dated Apr. 20, 2004 for International Application No. PCT/SE2003/001957.
International-Type Search Report dated Sep. 10, 2003 for International Application No. PCT/SE2003/001957.
Database WPI, Week 199833, Derwent Publications Ltd. London GB; AN 1998-381360 & JP 10152622 A (Dainippon Ink & Chem Inc) Jun. 9, 1998 Abstract.
STN International file Caplus, Caplus accession No. 2000:128495, Document No. 132:252449, Hinks, David et al: "Synthesis and evaluation of organic pigments and intermediates.1. Nonmutagenic benzidine analogs"; & Dyes and Pigments (2000), 44(3), 199-207.

* cited by examiner

Primary Examiner—James O Wilson
Assistant Examiner—Jeffrey H Murray
(74) Attorney, Agent, or Firm—Kenneth F. Mitchell

(57) ABSTRACT

The present invention relates to new compounds of formula (I) wherein Z is N; Y is $CONR^5$, $NR^5CO$, $SO_2NR^5$, $NR^5SO_2$, $CH_2NR^5$, $NR^5$, $NR^5CONR^5$, $CH_2CO$, $CO$, $O$ or $CH_2O$; X is CH or N; P is phenyl or a 5 or 6 membered heteroaromatic ring containing one or more heteroatoms selected from N, O or S and said phenyl ring or 5 or 6 membered heteroaromatic ring may optionally be fused with a 5 or 6 membered saturated, partially saturated or unsaturated ring containing one or more atoms selected from C, N, O or S; Q is $C_{1-6}$alkyl, $C_{2-6}$alkenyl or $C_{2-6}$alkynyl, a process for their preparation and new intermediates used therein, pharmaceutical formulations containing said therapeutically active compounds and to the use of said active compounds in therapy, such as provide compounds having a selective inhibiting effect at GSK3.

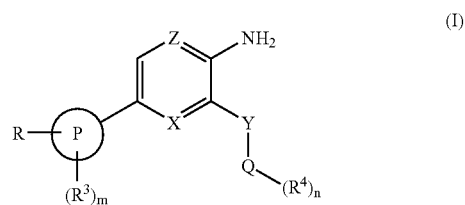

(I)

7 Claims, No Drawings

COMPOUNDS HAVING SELECTIVE INHIBITING EFFECT AT GSK3

FIELD OF THE INVENTION

The present invention relates to new compounds of formula I, as a free base or a pharmaceutically acceptable salt, solvate or solvate of salt thereof, to pharmaceutical formulations containing said compounds and to the use of said compounds in therapy. The present invention further relates to processes for the preparation of compounds of formula I and to new intermediates used in the preparation thereof.

BACKGROUND OF THE INVENTION

Glycogen synthase kinase 3 (GSK3) is a serine/threonine protein kinase composed of two isoforms (α and β), which are encoded by distinct genes but are highly homologous within the catalytic domain. GSK3 is highly expressed in the central and peripheral nervous system. GSK3 phosphorylates several substrates including tau, β-catenin, glycogen synthase, pyruvate dehydrogenase and elongation initiation factor 2b (eIF2b). Insulin and growth factors activate protein kinase B, which phosphorylates GSK3 on serine 9 residue and inactivates it.

Alzheimer's Disease (AD) Dementias, and Taupathies.

AD is characterized by cognitive decline, cholinergic dysfunction and neuronal death, neurofibrillary tangles and senile plaques consisting of amyloid-β deposits. The sequence of these events in AD is unclear, but is believed to be related. Glycogen synthase kinase 3β (GSK3β) or Tau (τ) phosphorylating kinase selectively phosphorylates the microtubule associated protein τ in neurons at sites that are hyperphosphorylated in AD brains. Hyperphosphorylated protein τ has lower affinity for microtubules and accumulates as paired helical filaments, which are the main components that constitute neurofibrillary tangles and neuropil threads in AD brains. This results in depolymerization of microtubules, which leads to dying back of axons and neuritic dystrophy. Neurofibrillary tangles are consistently found in diseases such as AD, amyotrophic lateral sclerosis, parkinsonism-dementia of Gaum, corticobasal degeneration, dementia pugilistica and head trauma, Down's syndrome, postencephalatic parkinsonism, progressive supranuclear palsy, Niemann-Pick's Disease and Pick's Disease. Addition of amyloid-β to primary hippocampal cultures results in hyperphosphorylation of τ and a paired helical filaments-like state via induction of GSK3β activity, followed by disruption of axonal transport and neuronal death (Imahori and Uchida., J. Biochem 121: 179-188, 1997). GSK3β preferentially labels neurofibrillary tangles and has been shown to be active in pre-tangle neurons in AD brains. GSK3 protein levels are also increased by 50% in brain tissue from AD patients. Furthermore, GSK3β phosphorylates pyruvate dehydrogenase, a key enzyme in the glycolytic pathway and prevents the conversion of pyruvate to acetyl-Co-A (Hoshi et al., PNAS 93:2719-2723, 1996). Acetyl-Co-A is critical for the synthesis of acetylcholine, a neurotransmitter with cognitive functions. Thus, GSK3β inhibition may have beneficial effects in progression as well as the cognitive deficits associated with Alzheimer's disease and other above-referred to diseases.

Chronic and Acute Neurodegenerative Diseases.

Growth factor mediated activation of the PI3K/Akt pathway has been shown to play a key role in neuronal survival. The activation of this pathway results in GSK3β inhibition. Recent studies (Bhat et. al., PNAS 97:11074-11079 (2000)) indicate that GSK3β activity is increased in cellular and animal models of neurodegeneration such as cerebral ischemia or after growth factor deprivation. For example, the active site phosphorylation was increased in neurons vulnerable to apoptosis, a type of cell death commonly thought to occur in chronic and acute degenerative diseases such as Alzheimer's Disease, Parkinson's Disease, amyotrophic lateral sclerosis, Huntington's Disease and HIV dementia, ischemic stroke and head trauma. Lithium was neuroprotective in inhibiting apoptosis in cells and in the brain at doses that resulted in the inhibition of GSK3β. Thus GSK3β inhibitors could be useful in attenuating the course of neurodegenerative diseases.

Bipolar Disorders (BD)

Bipolar Disorders are characterised by manic episodes and depressive episodes. Lithium has been used to treat BD based on its mood stabilising effects. The disadvantage of lithium is the narrow therapeutic window and the danger of overdosing that can lead to lithium intoxication. The recent discovery that lithium inhibits GSK3 at therapeutic concentrations has raised the possibility that this enzyme represents a key target of lithium's action in the brain (Stambolic et al., Curr. Biol. 6:1664-1668, 1996; Klein and Melton; PNAS 93:8455-8459, 1996). Inhibition of GSK3β may therefore be of therapeutic relevance in the treatment of BD as well as in AD patients that have affective disorders.

Schizophrenia

GSK3 is involved in signal transduction cascades of multiple cellular processes, particularly during neural development. Kozlovsky et al (Am J Psychiatry 2000 May;157(5): 831-3) found that GSK3β levels were 41% lower in the schizophrenic patients than in comparison subjects. This study indicates that schizophrenia involves neurodevelopmental pathology and that abnormal GSK3 regulation could play a role in schizophrenia. Furthermore, reduced β-catenin levels have been reported in patients exhibiting schizophrenia (Cotter et al., Neuroreport 9:1379-1383 (1998)).

Diabetes

Insulin stimulates glycogen synthesis in skeletal muscles via the dephosphorylation and thus activation of glycogen synthase. Under resting conditions, GSK3 phosphorylates and inactivates glycogen synthase via dephosphorylation. GSK3 is also over-expressed in muscles from Type II diabetic patients (Nikoulina et al., Diabetes 2000 February;49(2):263-71). Inhibition of GSK3 increases the activity of glycogen synthase thereby decreasing glucose levels by its conversion to glycogen. GSK3 inhibition may therefore be of therapeutic relevance in the treatment of Type I and Type II diabetes, diabetic neuropathy and diabetes related disorders.

Hair Loss

GSK3 phosphorylates and degrades β-catenin. β-catenin is an effector of the pathway for keratonin synthesis. (3-catenin stabilisation may be lead to increase hair development. Mice expressing a stabilised 13-catenin by mutation of sites phosphorylated by GSK3 undergo a process resembling de novo hair morphogenesis (Gat et al., Cell 1998 Nov. 25;95 (5):605-14)). The new follicles formed sebaceous glands and dermal papilla, normally established only in embryogenesis. Thus GSK3 inhibition may offer treatment for baldness.

Oral Contraceptives

Vijajaraghavan et al. (Biol Reprod 2000 June; 62 (6):1647-54) reported that GSK3 is high in motile versus immotile sperm. Immunocytochemistry revealed that GSK3 is present in the flagellum and the anterior portion of the sperm head. These data suggest that GSK3 could be a key element underlying motility initiation in the epididymis and regulation of mature sperm function. Inhibitors of GSK3 could be useful as contraceptives for males.

DISCLOSURE OF THE INVENTION

The object of the present invention is to provide compounds having a selective inhibiting effect at GSK3 as well as having a good bioavailability. Accordingly, the present invention provides a compound of formula I:

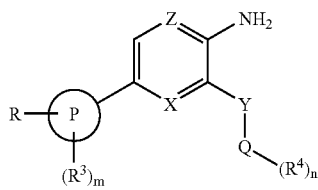

wherein:

$Z$ is $N$;

$Y$ is $CONR^5$, $NR^5CO$, $SO_2NR^5$, $NR^5SO_2$, $CH_2NR^5$, $NR^5CONR^5$, $CH_2CO$, $CO$ or $CH_2O$;

$X$ is $CH$ or $N$;

$P$ is phenyl or a 5 or 6 membered heteroaromatic ring containing one or more heteroatoms selected from N, O or S and said phenyl ring or 5 or 6 membered heteroaromatic ring may optionally be fused with a 5 or 6 membered saturated, partially saturated or unsaturated ring containing atoms independently selected from C, N, O or S;

$Q$ is $C_{1-6}$alkyl, $C_{2-6}$alkenyl or $C_{2-6}$alkynyl;

$R$ is CHO, fluoromethoxy, difluoromethoxy, trifluoromethoxy, $C_{0-6}$alkyl($SO_2$)$NR^1R^2$, $OC_{0-6}$alkyl($SO_2$)$NR^1R^2$, $OC_{1-6}$alkyl(SO)$NR^1R^2$, $C_{1-6}$alkyl(SO)$NR^1R^2$, $C_{0-6}$alkyl$NR^1$(SO)$R^2$, $OC_{1-6}$alkyl$NR^1$(SO)$R^2$, $C_{0-6}$alkyl$NR^1$($SO_2$)$NR^1R^2$, $OC_{1-6}$alkyl$NR^1$($SO_2$)$R^2$, $C_{0-6}$alkyl($SO_2$)$C_{1-6}$alkyl$NR^1R^2$, $OC_{0-6}$alkyl($SO_2$)$C_{1-6}$alkyl$NR^1R^2$, $C_{0-6}$alkyl(SO)$C_{1-6}$alkyl$NR^1R^2$, $OC_{1-6}$alkyl(SO)$C_{1-6}$alkyl$NR^1R^2$, $C_{0-6}$alkylSC$_{1-6}$alkyl$NR^1R^2$, $OC_{1-6}$alkylSC$_{1-6}$alkyl$NR^1R^2$, $OC_{1-6}$alkylOC$_{1-6}$alkyl, $C_{1-6}$alkylOC$_{1-6}$alkyl$NR^1R^2$, $OC_{1-6}$alkylOC$_{1-6}$alkyl$NR^1R^2$, $C_{0-6}$alkylCONR$^{10}$R$^{11}$, $OC_{0-6}$alkylCONR$^1$R$^2$, $OC_{1-6}$alkyl$NR^1R^2$, $C_{0-6}$alkyl$NR^{10}$(CO)R$^{11}$, $OC_{1-6}$alkyl$NR^1$(CO)R$^2$, $C_{0-6}$alkyl$NR^{11}$(CO)R$^{10}$, $C_{0-6}$alkylCOR$^{11}$, $OC_{1-6}$alkylCOR$^1$, $C_{0-6}$alkyl$NR^{10}$R$^{11}$, $C_{0-6}$alkylO(CO)R$^{11}$, $OC_{1-6}$ alkylO(CO)R$^1$, $C_{0-6}$alkylC(NR$^{10}$)NR$^{10}$R$^{11}$, $C_{0-6}$alkylC(NR$^{11}$)N(R$^{10}$)$_2$, $OC_{0-6}$alkylC(NR)NR$^1$R$^2$, $C_{0-6}$alkyl$NR^{10}$(CO)OR$^{11}$, $OC_{1-6}$alkyl$NR^1$(CO)OR$^2$, $C_{0-6}$alkyl$NR^{11}$(CO)OR$^{10}$, $OC_{1-6}$alkylCN, $NR^1$OR$^2$, $C_{0-6}$alkyl(CO)OR$^8$, $OC_{1-6}$ alkyl(CO)OR$^1$, $NR^1$(CO) $NR^1R^2$, $NR^1$(CO)(CO)R$^2$, $NR^1$(CO)(CO)$NR^1R^2$, OR$^{12}$ or SO$_3$R$^1$;

$R^1$ and $R^2$ are independently selected from hydrogen, $C_{1-6}$alkyl, $C_{2-6}$alkenyl, $C_{2-6}$alkynyl, $C_{0-6}$alkylC$_{3-6}$cycloalkyl, $C_{0-6}$alkylheterocycloalkyl, $C_{1-6}$alkyl$NR^6R^7$, $C_{0-6}$alkylaryl and $C_{0-6}$alkylheteroaryl, wherein any $C_{1-6}$alkyl, $C_{2-6}$alkenyl, $C_{2-6}$alkynyl, $C_{0-6}$alkylC$_{3-6}$cycloalkyl, $C_{0-6}$alkylheterocycloalkyl, $C_{0-6}$alkylaryl, $C_{0-6}$alkylheteroaryl may be substituted by one or more A;

$R^1$ and $R^2$ may together form a substituted 5 or 6 membered heterocyclic ring containing one or more heteroatoms independently selected from N, O or S, which heterocyclic ring may be optionally substituted by A;

$R^3$ is independently selected from halogen, nitro, CHO, $C_{0-6}$alkylCN, OC$_{1-6}$alkylCN, $C_{0-6}$alkylOR$^6$, OC$_{1-6}$alkylOR$^6$, fluoromethyl, difluoromethyl, trifluoromethyl, fluoromethoxy, difluoromethoxy, trifluoromethoxy, $C_{0-6}$alkyl$NR^6R^7$, OC$_{1-6}$alkyl$NR^6R^7$, OC$_{1-6}$alkylOC$_{1-6}$alkyl$NR^6R^7$, $NR^6$OR$^7$, $C_{0-6}$alkylCO$_2$R$^6$, OC$_{1-6}$alkylCO$_2$R$^6$, $C_{0-6}$alkylCONR$^6$R$^7$, OC$_{1-6}$alkylCONR$^6$R$^7$, OC$_{1-6}$alkyl$NR^6$(CO)R$^7$, $C_{0-6}$alkyl$NR^6$(CO)R$^7$, O(CO)$NR^6R^7$, $NR^6$(CO)OR$^7$, $NR^6$(CO)$NR^6R^7$, O(CO)OR$^6$, O(CO)R$^6$, $C_{0-6}$alkylCOR$^6$, OC$_{1-6}$alkylCOR$^6$, $NR^6$(CO)(CO)R$^6$, $NR^6$(CO)(CO)$NR^6R^7$, SR$^6$, $C_{0-6}$alkyl(SO$_2$)$NR^6R^7$, OC$_{1-6}$alkyl$NR^6$(SO$_2$)R$^7$, OC$_{0-6}$alkyl(SO$_2$)$NR^6R^7$, $C_{0-6}$alkyl(SO)$NR^6R^7$, OC$_{1-6}$alkyl(SO)$NR^6R^7$, SO$_3$R$^6$, $C_{0-6}$alkyl$NR^6$(SO$_2$)$NR^6R^7$, $C_{0-6}$alkyl$NR^6$(SO)R$^7$, OC$_{1-6}$alkyl$NR^6$(SO)R$^7$, OC$_{0-6}$alkylSO$_2$R$^6$, $C_{0-6}$alkylSO$_2$R$^6$, $C_{0-6}$alkylSOR$^6$, $C_{1-6}$alkyl, $C_{2-6}$alkenyl, $C_{2-6}$alkynyl, $C_{0-6}$alkylC$_{3-6}$cycloalkyl, $C_{0-6}$alkylaryl and $C_{0-6}$alkylheteroaryl, wherein any $C_{1-6}$alkyl, $C_{2-6}$alkenyl, $C_{2-6}$alkynyl, $C_{0-6}$alkylC$_{3-6}$cycloalkyl, $C_{0-6}$alkylaryl and $C_{0-6}$alkylheteroaryl may be optionally substituted by one or more A;

$R^4$ is independently selected from halogen, nitro, CHO, CN, OC$_{1-6}$alkylCN, OR$^6$, OC$_{1-6}$alkylOR$^6$, fluoromethyl, difluoromethyl, trifluoromethyl, fluoromethoxy, difluoromethoxy, trifluoromethoxy, $NR^6R^7$, OC$_{1-6}$alkyl$NR^6R^7$, $NR^6$OR$^7$, CO$_2$R$^6$, OC$_{1-6}$alkylCO$_2$R$^6$, CONR$^6$R$^7$, OC$_{1-6}$alkylCONR$^6$R$^7$, OC$_{1-6}$alkyl$NR^6$(CO)R$^7$, $NR^6$(CO)R$^7$, O(CO)$NR^6R^7$, $NR^6$(CO)OR$^7$, $NR^6$(CO)$NR^6R^7$, O(CO)OR$^6$, O(CO)R$^6$, COR$^6$, OC$_{1-6}$alkylCOR$^6$, $NR^6$(CO)(CO)R$^6$, $NR^6$(CO)(CO)$NR^6R^7$, SR$^6$, (SO$_2$)$NR^6R^7$, OC$_{1-6}$alkyl$NR^6$(SO$_2$)R$^7$, OC$_{0-6}$alkyl(SO$_2$)$NR^6R^7$, (SO)$NR^6R^7$, OC$_{1-6}$alkyl(SO)$NR^6R^7$, SO$_3$R$^6$, $NR^6$(SO$_2$)$NR^6R^7$, $NR^6$(SO)R$^7$, OC$_{1-6}$alkyl$NR^6$(SO)R$^7$, OC$_{0-6}$alkylSO$_2$R$^6$, SO$_2$R$^6$, SOR$^6$, $C_{3-6}$cycloalkyl, phenyl, a 5 or 6 membered heteroaromatic ring containing one or more heteroatoms independently selected from N, O, or S, or a 5 or 6 membered heterocyclic ring containing one or more heteroatoms independently selected from N, O, or S which heterocyclic group may be saturated or unsaturated, and said phenyl ring or 5 or 6 membered heteroaromatic ring or 5 or 6 membered heterocyclic ring may optionally be fused with a 5 or 6 membered saturated, partially saturated or unsaturated ring containing atoms independently selected from C, N, O or S wherein any $C_{3-6}$cycloalkyl, phenyl, 5 or 6 membered heteroaromatic ring with one or two heteroatoms selected independently from N, O, or S or a 5 or 6 membered heterocyclic ring containing one or two heteroatoms selected independently from N, O, or S; may be optionally be substituted by one or more A;

m is 0, 1, 2, 3 or 4;

n is 0, 1, 2, 3 or 4;

$R^5$ is hydrogen or $C_{1-6}$alkyl $R^6$ and $R^7$ are independently selected from hydrogen, $C_{1-6}$alkyl, $C_{2-6}$alkenyl, $C_{2-6}$alkynyl, $C_{0-6}$alkylC$_{3-6}$cycloalkyl, $C_{0-6}$alkylaryl, $C_{0-6}$alkylheteroaryl and $C_{1-6}$alkyl$NR^8R^9$;

$R^6$ and $R^7$ may together form a substituted 5 or 6 membered heterocyclic ring containing one or more heteroatoms independently selected from N, O or S, which heterocyclic ring may be optionally substituted by A and wherein a CH$_2$ group may optionally be replaced by a CO group;

$R^8$ and $R^9$ are independently selected from hydrogen, $C_{1-6}$alkyl, $C_{2-6}$alkenyl, $C_{2-6}$alkynyl, $C_{0-6}$alkyl$C_{3-6}$cycloalkyl, $C_{0-6}$alkylaryl and $C_{0-6}$alkylheteroaryl;

$R^8$ and $R^9$ may together form a 5 or 6 membered heterocyclic ring containing one or more heteroatoms selected from N, O or S, which heterocyclic ring may be optionally substituted by A;

$R^{10}$ is hydrogen, $C_{1-6}$alkyl, $C_{2-6}$alkenyl, $C_{2-6}$alkynyl, $C_{0-6}$alkyl$C_{3-6}$cycloalkyl, $C_{0-6}$alkylaryl, $C_{0-6}$alkylheteroaryl or $C_{1-6}$alkylNR$^8$R$^9$;

$R^{11}$ is $C_{1-6}$alkylNR$^8$R$^9$;

$R^{10}$ and $R^{11}$ may together form a 5 or 6 membered heterocyclic ring containing one or more heteroatoms selected from N, O or S, which heterocyclic ring may be optionally substituted by A;

$R^{12}$ is a 5 or 6 membered heterocyclic ring containing one or more heteroatoms independently selected from N, O or S, which heterocyclic ring may be optionally substituted by A; wherein any $C_{1-6}$alkyl, $C_{2-6}$alkenyl, $C_{2-6}$alkyl, $C_{0-6}$alkyl$C_{3-6}$cycloalkyl, $C_{0-6}$alkylheterocycloalkyl, $C_{0-6}$alkylaryl, $C_{0-6}$alkylheteroaryl defined under $R^5$ to $R^{12}$ may be substituted by one or more A;

A is halogen, nitro, oxo (=O), CHO, CN, OR$^6$, $C_{1-6}$alkyl, $C_{2-6}$alkenyl, $C_{2-6}$alkynyl, $C_{0-6}$alkyl$C_{3-6}$cycloalkyl, fluoromethyl, difluoromethyl, trifluoromethyl, fluoromethoxy, difluoromethoxy, trifluoromethoxy, $C_{0-6}$alkylNR$^6$R$^7$, OC$_{1-6}$alkylNR$^6$R$^7$, CO$_2$R$^8$, CONR$^6$R$^7$, NR$^6$(CO)R$^6$, O(CO)R$^6$, COR$^6$, SR$^6$, (SO$_2$)NR$^6$R$^7$, (SO)NR$^6$R$^7$, SO$_3$R$^6$, SO$_2$R$^6$ or SOR$^6$;

as a free base or a pharmaceutically acceptable salt, solvate or solvate of a salt thereof.

One aspect of the invention relates to compounds of formula I, wherein wherein Z and X is N; P is phenyl; R is $C_{0-6}$alkyl(SO$_2$)NR$^1$R$^2$; and m is 0.

In one embodiment of this aspect, $R^1$ and $R^2$ in $C_{0-6}$alkyl(SO$_2$)NR$^1$R$^2$ together form a substituted 5 or 6 membered heterocyclic ring containing one or more heteroatoms selected from N, O or S.

In another embodiment of this aspect, there are provided such compounds wherein said heterocyclic ring comprises one or more N heteroatoms and said heterocyclic ring is optionally substituted by A, preferably a $C_{1-6}$alkyl.

Another aspect of the invention relates to compounds of formula I, wherein Y is CONR$^5$; $R^5$ is hydrogen; Q is $C_{1-6}$alkyl; $R^4$ is selected from: phenyl, a 5 or 6 membered heteroaromatic ring containing one or more heteroatoms independently selected from N, O, or S or a 5 or 6 membered heterocyclic ring containing one or two heteroatoms selected independently from N, O, or S which heterocyclic group may be saturated or unsaturated, CN, OR$^6$, SO$_2$R$^6$, NR$^6$(CO)R$^7$, (SO$_2$)NR$^6$R$^7$, and CONR$^6$R$^7$; and n is 1; said phenyl, 5 or 6 membered heteroaromatic ring or 5 or 6 membered heterocyclic ring may optionally be substituted by A.

One embodiment of this aspect relates to compounds wherein A is selected from OR$^6$, $C_{1-6}$alkyl, oxo (=O) and nitro; and R$^6$ and/or R$^7$ are selected from $C_{1-6}$alkyl and hydrogen.

In a further aspect of the invention the following compounds are provided:

3-Amino-N-(2-cyanoethyl)-6-[4-(pyrrolidin-1-ylsulfonyl)phenyl]pyrazine-2-carboxamide;

3-Amino-N-(3-amino-3-oxopropyl)-6-[4-(pyrrolidin-1-ylsulfonyl)phenyl]pyrazine-2-carboxamide;

3-Amino-N-(2-nitrobenzyl)-6-[4-(pyrrolidin-1-ylsulfonyl)phenyl]pyrazine-2-carboxamide;

3-Amino-N-(2-methoxybenzyl)-6-[4-(pyrrolidin-1-ylsulfonyl)phenyl]pyrazine-2-carboxamide;

3-Amino-N-(3-morpholin-4-ylpropyl)-6-[4-(pyrrolidin-1-ylsulfonyl)phenyl]pyrazine-2-carboxamide;

3-Amino-N-[3-(4-methylpiperazin-1-yl)propyl]-6-[4-(pyrrolidin-1-ylsulfonyl)phenyl]pyrazine-2-carboxamide;

as a free base or a pharmaceutically acceptable salt, solvate or solvate of a salt thereof, 3-Amino-N-(2-morpholin-4-ylethyl)-6-[(pyrrolidin-1-ylsulfonyl)phenyl]pyrazine-2-carboxamide hydrochloride;

3-Amino-N-[2-(1H-imidazol-4-yl)ethyl]-6-[4-(pyrrolidin-1-ylsulfonyl)phenyl]pyrazine-2-carboxamide hydrochloride;

3-Amino-N-[3-(1H-imidazol-1-yl)propyl]-6-[4-(pyrrolidin-1-ylsulfonyl)phenyl]pyrazine-2-carboxamide hydrochloride;

3-Amino-6-{4-[(4-methylpiperazin-1-yl)sulfonyl]phenyl}-N-(2-thien-2-ylethyl)pyrazine-2-carboxamide hydrochloride;

3-Amino-6-{4-[(4-methylpiperazin-1-yl)sulfonyl]phenyl}-N-(thien-2-ylmethyl)pyrazine-2-carboxamide hydrochloride;

3-Amino-N-(2-methoxyethyl)-6-{4-[(4-methylpiperazin-1-yl)sulfonyl]phenyl}pyrazine-2-carboxamide hydrochloride;

3-Amino-N-(3-methoxypropyl)-6-{4-[(4-methylpiperazin-1-yl)sulfonyl]phenyl}pyrazine-2-carboxamide hydrochloride;

3-Amino-6-{4-[(4-methylpiperazin-1-yl)sulfonyl]phenyl}-N-[3-(2-oxopyrrolidin-1-yl)propyl]pyrazine-2-carboxamide hydrochloride;

3-Amino-N-(cyanomethyl)-6-{4-[(4-methylpiperazin-1-yl)sulfonyl]phenyl}pyrazine-2-carboxamide dihydrochloride;

3-Amino-6-[4-[(4-methyl-1-piperazinyl)sulfonyl]phenyl]-N-[2-(1H-pyrrol-1-yl)ethyl]-2-pyrazinecarboxamide hydrochloride;

3-Amino-6-[4-[(4-methyl-1-piperazinyl)sulfonyl]phenyl]-N-[2-(methylsulfonyl)ethyl]-2-pyrazinecarboxamide hydrochloride;

N-[2-(Acetylamino)ethyl]-3-amino-6-[4-[(4-methyl-1-piperazinyl)sulfonyl]phenyl]-2-pyrazinecarboxamide hydrochloride;

3-Amino-6-[4-[(4-methyl-1-piperazinyl)sulfonyl]phenyl]-N-[2-(2-oxo-1-imidazolidinyl)ethyl]-2-pyrazinecarboxamide hydrochloride;

3-Amino-N-[2-(aminosulfonyl)ethyl]-6-[4-[(4-methyl-1-piperazinyl)sulfonyl]phenyl]-2-pyrazinecarboxamide hydrochloride;

or as a free base or an alternative pharmaceutically acceptable salt, solvate or solvate of a salt thereof.

Another aspect of the invention is the compounds of formulas XIXa, IV, XXII, which are useful as intermediates in the preparation of compounds of formula I.

A compound of formula XIXa

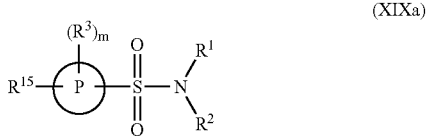

(XIXa)

wherein

P is phenyl $R^1$ and $R^2$ are independently selected from hydrogen, $C_{1-6}$alkyl, $C_{2-6}$alkenyl, $C_{2-6}$alkynyl, $C_{0-6}$alkyl$C_{3-6}$cycloalkyl, $C_{0-6}$alkylheterocycloalkyl, $C_{1-6}$alkyl$NR^6R^7$, $C_{0-6}$alkylaryl and $C_{0-6}$alkylheteroaryl, wherein any $C_{1-6}$alkyl, $C_{2-6}$alkenyl, $C_{2-6}$alkynyl, $C_{0-6}$alkyl$C_{3-6}$cycloalkyl, $C_{0-6}$alkylheterocycloalkyl, $C_{0-6}$alkylaryl, $C_{0-6}$alkylheteroaryl may be substituted by one or more A;

$R^1$ and $R^2$ may together form a substituted 5 or 6 membered heterocyclic ring containing one or more heteroatoms independently selected from N, O or S, which heterocyclic ring may be optionally substituted by A;

$R^3$ is independently selected from halogen, nitro, CHO, $C_{0-6}$alkylCN, $OC_{1-6}$alkylCN, $C_{0-6}$alkyl$OR^6$, $OC_{1-6}$alkyl$OR^6$, fluoromethyl, difluoromethyl, trifluoromethyl, fluoromethoxy, difluoromethoxy, trifluoromethoxy, $C_{0-6}$alkyl$NR^6R^7$, $OC_{1-6}$alkyl$NR^6R^7$, $OC_{1-6}$alkyl$OC_{1-6}$alkyl$NR^6R^7$, $NR^6OR^7$, $C_{0-6}$alkyl$CO_2R^6$, $OC_{1-6}$alkyl$CO_2R^6$, $C_{0-6}$alkyl$CONR^6R^7$, $OC_{1-6}$alkyl$CONR^6R^7$, $OC_{1-6}$alkyl$NR^6(CO)R^7$, $CO_{0-6}$alkyl$NR^6(CO)R^7$, $O(CO)NR^6R^7$, $NR^6(CO)OR^7$, $NR^6(CO)NR^6R^7$, $O(CO)OR^6$, $O(CO)R^6$, $C_{0-6}$alkyl$COR^6$, $OC_{1-6}$alkyl$COR^6$, $NR^6(CO)(CO)R^6$, $NR^6(CO)(CO)NR^6R^7$, $SR^6$, $C_{0-6}$alkyl$(SO_2)NR^6R^7$, $OC_{1-6}$alkyl$NR^6(SO_2)R^7$, $OC_{0-6}$alkyl$(SO_2)NR^6R^7$, $C_{0-6}$alkyl$(SO)NR^6R^7$, $OC_{1-6}$alkyl$(SO)NR^6R^7$, $SO_3R^6$, $C_{0-6}$alkyl$NR^6(SO_2)NR^6R^7$, $C_{0-6}$alkyl$NR^6(SO)R^7$, $OC_{1-6}$alkyl$NR^6(SO)R^7$, $OC_{0-6}$alkyl$SO_2R^6$, $C_{0-6}$alkyl$SO_2R^6$, $C_{0-6}$alkyl$SOR^6$, $C_{1-6}$alkyl, $C_{2-6}$alkenyl, $C_{2-6}$alkynyl, $C_{0-6}$alkyl$C_{3-6}$cycloalkyl, $C_{0-6}$alkylaryl and $C_{0-6}$alkylheteroaryl, wherein any $C_{1-6}$alkyl, $C_{2-6}$alkenyl, $C_{2-6}$alkynyl, $C_{0-6}$alkyl$C_{3-6}$cycloalkyl, $C_{0-6}$alkylaryl and $C_{0-6}$alkylheteroaryl may be optionally substituted by one or more A;

$R^6$ and $R^7$ are independently selected from hydrogen, $C_{1-6}$alkyl, $C_{2-6}$alkenyl, $C_{2-6}$alkynyl, $C_{0-6}$alkyl$C_{3-6}$cycloalkyl, $C_{0-6}$alkylaryl, $C_{0-6}$alkylheteroaryl and $C_{1-6}$alkyl$NR^8R^9$;

$R^6$ and $R^7$ may together form a substituted 5 or 6 membered heterocyclic ring containing one or more heteroatoms independently selected from N, O or S, which heterocyclic ring may be optionally substituted by A and wherein a $CH_2$ group may optionally be replaced by a CO group;

$R^8$ and $R^9$ are independently selected from hydrogen, $C_{1-6}$alkyl, $C_{2-6}$alkenyl, $C_{2-6}$alkynyl, $C_{0-6}$alkyl$C_{3-6}$cycloalkyl, $C_{0-6}$alkylaryl and $C_{0-6}$alkylheteroaryl;

$R^8$ and $R^9$ may together form a 5 or 6 membered heterocyclic ring containing one or more heteroatoms selected from N, O or S, which heterocyclic ring may be optionally substituted by A;

m is 0, 1, 2, 3 or 4;

$R^{15}$ is a group outlined in Scheme I, wherein $R^{16}$ and $R^{17}$ are hydroxy and B is boron;

Scheme I. Examples but not limitations of $R^{15}$

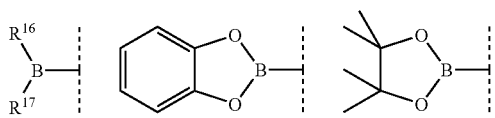

A is halogen, oxo (=O), nitro, CHO, CN, $OR^6$, $C_{1-6}$alkyl, $C_{2-6}$alkenyl, $C_{2-6}$alkynyl, $C_{0-6}$alkyl$C_{3-6}$cycloalkyl, fluoromethyl, difluoromethyl, trifluoromethyl, fluoromethoxy, difluoromethoxy, trifluoromethoxy, $C_{0-6}$alkyl$NR^6R^7$, $OC_{1-6}$alkyl$NR^6R^7$, $CO_2R^8$, $CONR^6R^7$, $NR^6(CO)R^6$, $O(CO)R^6$, $COR^6$, $SR^6$, $(SO_2)NR^6R^7$, $(SO)NR^6R^7$, $SO_3R^6$, $SO_2R^6$ or $SOR^6$;

as a free base or a salt, solvate or solvate of a salt thereof.

A compound of formula XIXa

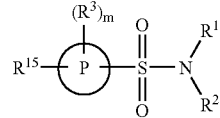

(XIXa)

wherein $R^1$ and $R^2$ together forms a substituted 5 or 6 membered heterocyclic ring containing one or more heteroatoms independently selected from N, O or S, which heterocyclic ring may be optionally substituted by A;

m is 0;

A is $C_{1-6}$alkyl;

as a free base or a salt, solvate or solvate of a salt thereof.

A compound of formula IV

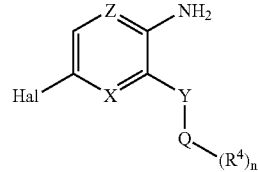

(IV)

wherein

Y is $CONR^5$, $NR^5CO$, $SO_2NR^5$, $NR^5SO_2$, $CH_2NR^5$$NR^5CONR^5$, $CH_2CO$, CO or $CH_2O$;

X is CH or N;

Z is N;

Q is $C_{1-6}$alkyl, $C_{2-6}$alkenyl or $C_{2-6}$alkynyl;

$R^4$ is independently selected from halogen, nitro, CHO, CN, $OC_{1-6}$alkylCN, $OR^6$, $OC_{1-6}$alkyl$OR^6$, fluoromethyl, difluoromethyl, trifluoromethyl, fluoromethoxy, difluoromethoxy, trifluoromethoxy, $NR^6R^7$, $OC_{1-6}$alkyl$NR^6R^7$, $NR^6OR^7$, $CO_2R^6$, $OC_{1-6}$alkyl$CO_2R^6$, $CONR^6R^7$, $OC_{1-6}$alkyl$CONR^6R^7$, $OC_{1-6}$alkyl$NR^6(CO)R^7$, $NR^6(CO)R^7$, $O(CO)NR^6R^7$, $NR^6(CO)OR^7$, $NR^6(CO)NR^6R^7$, $O(CO)OR^6$, $O(CO)R^6$, $COR^6$, $OC_{1-6}$alkyl$COR^6$, $NR^6(CO)(CO)R^6$, $NR^6(CO)(CO)NR^6R^7$, $SR^6$, $(SO_2)NR^6R^7$, $OC_{1-6}$alkyl$NR^6(SO_2)R^7$, $OC_{0-6}$alkyl$(SO_2)NR^6R^7$, $(SO)NR^6R^7$, $OC_{1-6}$alkyl$(SO)NR^6R^7$, $SO_3R^6$, $NR^6(SO_2)NR^6R^7$, $NR^6(SO)R^7$, $OC_{1-6}$alkyl$NR^6(SO)R^7$, $OC_{0-6}$alkyl$SO_2R^6$, $SO_2R^6$, $SOR^6$, $C_{3-6}$cycloalkyl, phenyl, a 5 or 6 membered heteroaromatic ring containing one or more heteroatoms independently selected from N, O, or S, or a 5 or 6 membered heterocyclic ring containing one or more heteroatoms independently selected from N, O, or S which heterocyclic group may be saturated or unsaturated, and said phenyl ring or 5 or 6 membered heteroaromatic ring or 5 or 6 membered heterocyclic ring may optionally be fused with a 5 or 6 membered saturated, partially saturated or unsaturated ring containing atoms independently selected from C, N, O or S wherein any $C_{3-6}$cycloalkyl, phenyl, 5 or 6 membered heteroaromatic ring with one or two heteroatoms selected independently from N, O, or S or a 5 or 6 membered heterocyclic ring containing one or two heteroatoms selected independently from N, O, or S; may be optionally be substituted by one or more A;
is $R^5$ is hydrogen or $C_{1-6}$alkyl
$R^6$ and $R^7$ are independently selected from hydrogen, $C_{1-6}$alkyl, $C_{2-6}$alkenyl, $C_{2-6}$alkynyl, $C_{0-6}$alkyl$C_{3-6}$cycloalkyl, $C_{0-6}$alkylaryl, $C_{0-6}$alkylheteroaryl and $C_{1-6}$alkylNR$^8$R$^9$;
$R^6$ and $R^7$ may together form a substituted 5 or 6 membered heterocyclic ring containing one or more heteroatoms independently selected from N, O or S, which heterocyclic ring may be optionally substituted by A and wherein a CH$_2$ group may optionally be replaced by a CO group;
$R^8$ and $R^9$ are independently selected from hydrogen, $C_{1-6}$alkyl, $C_{2-6}$alkenyl, $C_{2-6}$alkynyl, $C_{0-6}$alkyl$C_{3-6}$cycloalkyl, $C_{0-6}$alkylaryl and $C_{0-6}$alkylheteroaryl;
$R^8$ and $R^9$ may together form a 5 or 6 membered heterocyclic ring containing one or more heteroatoms selected from N, O or S, which heterocyclic ring may be optionally substituted by A;
Hal is halogen;
n is 0, 1, 2, 3 or 4;
A is halogen, oxo (=O), nitro, CHO, CN, OR$^6$, $C_{1-6}$alkyl, $C_{2-6}$alkenyl, $C_{2-6}$alkynyl, $C_{0-6}$alkyl$C_{3-6}$cycloalkyl, fluoromethyl, difluoromethyl, trifluoromethyl, fluoromethoxy, difluoromethoxy, trifluoromethoxy, $C_{0-6}$alkylNR$^6$R$^7$, OC$_{1-6}$alkylNR$^6$R$^7$, CO$_2$R$^8$, CONR$^6$R$^7$, NR$^6$(CO)R$^6$, O(CO)R$^6$, COR$^6$, SR$^6$, (SO$_2$)NR$^6$R$^7$, (SO)NR$^6$R$^7$, SO$_3$R$^6$, SO$_2$R$^6$ or SOR$^6$;

as a free base or a salt, solvate or solvate of a salt thereof.
A compound of formula IV

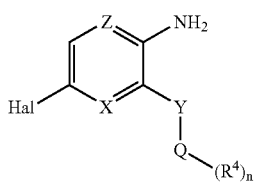

(IV)

wherein
Y is CONR$^5$;
X is N;
Z is N;
Q is $C_{1-6}$alkyl;
$R^4$ is independently selected from CN, OR$^6$, a 5 or 6 membered heteroaromatic ring containing one or more heteroatoms independently selected from N, O, or S, or a 5 or 6 membered heterocyclic ring containing one or more heteroatoms independently selected is from N, O, or S which heterocyclic group may be saturated or unsaturated, wherein any 5 or 6 membered heterocyclic ring containing one or two heteroatoms selected independently from N, O, or S; may be optionally be substituted by A;

$R^5$ is hydrogen;
$R^6$ is, $C_{1-6}$alkyl;
n is 1;
A is oxo (=O);

as a free base or a salt, solvate or solvate of a salt thereof.
A compound of formula XXII

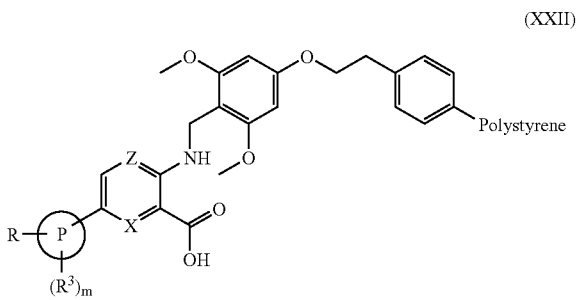

(XXII)

wherein:
Z is N;
X is CH or N;
P is phenyl or a 5 or 6 membered heteroaromatic ring containing one or more heteroatoms selected from N, O or S and said phenyl ring or 5 or 6 membered heteroaromatic ring may optionally be fused with a 5 or 6 membered saturated, partially saturated or unsaturated ring containing atoms independently selected from C, N, O or S;
R is CHO, fluoromethoxy, difluoromethoxy, trifluoromethoxy, $C_{0-6}$alkyl(SO$_2$)NR$^1$R$^2$, OC$_{0-6}$alkyl(SO$_2$)NR$^1$R$^2$, OC$_{1-6}$alkyl(SO)NR$^1$R$^2$, $C_{1-6}$alkyl(SO)NR$^1$R$^2$, $C_{0-6}$alkylNR$^1$(SO)R$^2$, OC$_{1-6}$alkylNR$^1$(SO)R$^2$, $C_{0-6}$alkylNR$^1$(SO$_2$)NR$^1$R$^2$, OC$_{1-6}$alkylNR$^1$(SO$_2$)R$^2$, $C_{0-6}$alkyl(SO$_2$)C$_{1-6}$alkylNR$^1$R$^2$, OC$_{0-6}$alkyl(SO$_2$)C$_{1-6}$alkylNR$^1$R$^2$, $C_{0-6}$alkyl(SO)C$_{1-6}$alkylNR$^1$R$^2$, OC$_{1-6}$alkyl(SO)C$_{1-6}$alkylNR$^1$R$^2$, $C_{0-6}$alkylSC$_{1-6}$alkylNR$^1$R$^2$, OC$_{1-6}$alkylSC$_{1-6}$alkylNR$^1$R$^2$, OC$_{1-6}$alkylOC$_{1-6}$alkyl, $C_{1-6}$alkylOC$_{1-6}$ alkylNR$^1$R$^2$, OC$_{1-6}$alkylOC$_{1-6}$alkylNR$^1$R$^2$, $C_{0-6}$alkylCONR$^{10}$R$^{11}$, OC$_{0-6}$alkylCONR$^1$R$^2$, OC$_{1-6}$alkylNR$^1$R$^2$, $C_{0-6}$alkylNR$^{10}$(CO)R$^{11}$, OC$_{1-6}$alkylNR$^1$(CO)R$^2$, $C_{0-6}$alkylNR$^{11}$(CO)R$^{10}$, $C_{0-6}$alkylCOR$^{11}$, OC$_{1-6}$alkylCOR$^1$, $C_{0-6}$alkylNR$^{10}$R$^{11}$, $C_{0-6}$alkylO(CO)R$^{11}$, OC$_{1-6}$ alkylO(CO)R$^1$, $C_{0-6}$alkylC(NR$^{10}$)NR$^{10}$R$^{11}$, $C_{0-6}$alkylC(NR$^{11}$)N(R$^{10}$)$_2$, OC$_{0-6}$alkylC(NR$^1$)NR$^1$R$^2$, $C_{0-6}$alkylNR$^{10}$(CO)OR$^{11}$, OC$_{1-6}$alkylNR$^1$(CO)OR$^2$, $C_{0-6}$alkylNR$^{11}$(CO)OR$^{10}$, OC$_{1-6}$alkylCN, NR$^1$OR$^2$, $C_{0-6}$alkyl(CO)OR$^8$, OC$_{1-6}$alkyl(CO)OR$^1$, NR$^1$(CO)NR$^1$R$^2$, NR$^1$(CO)(CO)R$^2$, NR$^1$(CO)(CO)NR$^1$R$^2$, OR$^{12}$ or SO$_3$R$^1$;
$R^1$ and $R^2$ are independently selected from hydrogen, $C_{1-6}$alkyl, $C_{2-6}$alkenyl, $C_{2-6}$alkynyl, $C_{0-6}$alkyl$C_{3-6}$cycloalkyl, $C_{0-6}$alkylheterocycloalkyl, $C_{1-6}$alkylNR$^6$R$^7$, $C_{0-6}$alkylaryl and $C_{0-6}$alkylheteroaryl, wherein any $C_{1-6}$alkyl, $C_{2-6}$alkenyl, $C_{2-6}$alkynyl, $C_{0-6}$alkyl$C_{3-6}$cycloalkyl, $C_{0-6}$alkylheterocycloalkyl, $C_{0-6}$alkylaryl, $C_{0-6}$alkylheteroaryl may be substituted by one or more A;
$R^1$ and $R^2$ may together form a substituted 5 or 6 membered heterocyclic ring containing one or more heteroatoms independently selected from N, O or S, which heterocyclic ring may be optionally substituted by A;
$R^3$ is independently selected from halogen, nitro, CHO, $C_{0-6}$alkylCN, OC$_{1-6}$alkylCN, $C_{0-6}$alkylOR$^6$, OC$_{1-6}$alkylOR$^6$, fluoromethyl, difluoromethyl, trifluoromethyl, fluoromethoxy, difluoromethoxy, trifluoromethoxy, $C_{0-6}$alkylNR$^6$R$^7$, OC$_{1-6}$alkylNR$^6$R$^7$, OC$_{1-6}$alkylOC$_{1-6}$alkylNR$^6$R$^7$, NR$^6$OR$^7$, C$_{0-6}$alkylCO$_2$R$^6$, OC$_{1-6}$alkylCO$_2$R$^6$, C$_{0-6}$alkylCONR$^6$R$^7$, OC$_{1-6}$alkylCONR$^6$R$^7$, OC$_{1-6}$alkylNR$^6$(CO)R$^7$, C$_{0-6}$alkylNR$^6$(CO)R$^7$, O(CO)NR$^6$R$^7$, NR$^6$(CO)OR$^7$, NR$^6$(CO)NR$^6$R$^7$, O(CO)OR$^6$, O(CO)R$^6$, C$_{0-6}$alkylCOR$^6$, OC$_{1-6}$alkylCOR$^6$, NR$^6$(CO)(CO)R$^6$, NR$^6$(CO)(CO)NR$^6$R$^7$, SR$^6$, C$_{0-6}$alkyl(SO$_2$)NR$^6$R$^7$, OC$_{1-6}$alkylNR$^6$(SO$_2$)R$^7$, OC$_{0-6}$alkyl(SO$_2$)NR$^6$R$^7$, C$_{0-6}$alkyl(SO)NR$^6$R$^7$, OC$_{1-6}$alkyl(SO)NR$^6$R$^7$, SO$_3$R$^6$, C$_{0-6}$alkylNR$^6$(SO$_2$)NR$^6$R$^7$, C$_{0-6}$alkylNR$^6$(SO)R$^7$, OC$_{1-6}$alkylNR$^6$(SO)R$^7$, OC$_{0-6}$alkylSO$_2$R$^6$, C$_{0-6}$alkylSO$_2$R$^6$, C$_{0-6}$alkylSOR$^6$, C$_{1-6}$alkyl, C$_{2-6}$alkenyl, C$_{2-6}$alkynyl, C$_{0-6}$alkylC$_{3-6}$cycloalkyl, C$_{0-6}$alkylaryl and C$_{0-6}$alkylheteroaryl, wherein any C$_{1-6}$alkyl, C$_{2-6}$alkenyl, C$_{2-6}$alkynyl, C$_{0-6}$alkylC$_{3-6}$cycloalkyl, C$_{0-6}$alkylaryl and C$_{0-6}$alkylheteroaryl may be optionally substituted by one or more A;

R$^6$ and R$^7$ are independently selected from hydrogen, C$_{1-6}$alkyl, C$_{2-6}$alkenyl, C$_{2-6}$alkynyl, C$_{0-6}$alkylC$_{3-6}$cycloalkyl, C$_{0-6}$alkylaryl, C$_{0-6}$alkylheteroaryl and C$_{1-6}$alkylNR$^8$R$^9$;

R$^6$ and R$^7$ may together form a substituted 5 or 6 membered heterocyclic ring containing one or more heteroatoms independently selected from N, O or S, which heterocyclic ring may be optionally substituted by A and wherein a CH$_2$ group may optionally be replaced by a CO group;

R$^8$ and R$^9$ are independently selected from hydrogen, C$_{1-6}$alkyl, C$_{2-6}$alkenyl, C$_{2-6}$alkynyl, C$_{0-6}$alkylC$_{3-6}$cycloalkyl, C$_{0-6}$alkylaryl and C$_{0-6}$alkylheteroaryl;

R$^8$ and R$^9$ may together form a 5 or 6 membered heterocyclic ring containing one or more heteroatoms selected from N, O or S, which heterocyclic ring may be optionally substituted by A;

R$^{10}$ is hydrogen, C$_{1-6}$alkyl, C$_{2-6}$alkenyl, C$_{2-6}$alkynyl, C$_{0-6}$alkylC$_{3-6}$cycloalkyl, C$_{0-6}$alkylaryl, C$_{0-6}$alkylheteroaryl or C$_{1-6}$alkylNR$^8$R$^9$;

R$^{11}$ is C$_{1-6}$alkylNR$^8$R$^9$;

R$^{10}$ and R$^{11}$ may together form a 5 or 6 membered heterocyclic ring containing one or more heteroatoms selected from N, O or S, which heterocyclic ring may be optionally substituted by A;

A is halogen, oxo (═O), nitro, CHO, CN, OR$^6$, C$_{1-6}$alkyl, C$_{2-6}$alkenyl, C$_{2-6}$alkynyl, C$_{0-6}$alkylC$_{3-6}$cycloalkyl, fluoromethyl, difluoromethyl, trifluoromethyl, fluoromethoxy, difluoromethoxy, trifluoromethoxy, C$_{0-6}$alkylNR$^6$R$^7$, OC$_{1-6}$alkylNR$^6$R$^7$, CO$_2$R$^8$, CONR$^6$R$^7$, NR$^6$(CO)R$^6$, O(CO)R$^6$, COR$^6$, SR$^6$, (SO$_2$)NR$^6$R$^7$, (SO)NR$^6$R$^7$, SO$_3$R$^6$, SO$_2$R$^6$ or SOR$^6$;

m is 0, 1, 2, 3 or 4;

as a free base or a salt, solvate or solvate of a salt thereof.

A compound of formula XXII

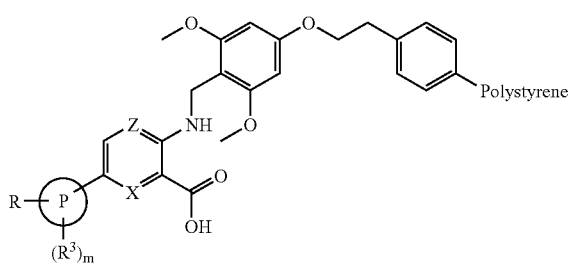

(XXII)

wherein:
Z is N;
X is N;
P is phenyl;
R is C$_{0-6}$alkyl(SO$_2$)NR$^1$R$^2$;
R$^1$ and R$^2$ may together form a substituted 5 or 6 membered heterocyclic ring containing one or more heteroatoms independently selected from N, O or S;
m is 0;

as a free base or a salt, solvate or solvate of a salt thereof.

In yet another aspect of the invention the following compounds, which are useful as intermediates in the preparation of compounds of formula I, are provided:

1-[(4-Bromophenyl)sulfonyl]pyrrolidine;
4-(Pyrrolidin-1-ylsulfonyl)phenylboronic acid;
4-[(4-Methylpiperazin-1-yl)sulfonyl]phenylboronic acid;
3-Amino-6-bromo-N-(2-morpholin-4-ylethyl)pyrazine-2-carboxamide;
3-Amino-6-bromo-N-[2-(1H-imidazol-4-yl)ethyl]pyrazine-2-carboxamide;
3-Amino-6-bromo-N-[3-(1H-imidazol-1-yl)propyl]pyrazine-2-carboxamide;
3-Amino-6-bromo-N-(2-thien-2-ylethyl)pyrazine-2-carboxamide;
3-Amino-6-bromo-N-(thien-2-ylmethyl)pyrazine-2-carboxamide;
3-Amino-6-bromo-N-(2-methoxyethyl)pyrazine-2-carboxamide;
3-Amino-6-bromo-N-(3-methoxypropyl)pyrazine-2-carboxamide;
3-Amino-6-bromo-N-[3-(2-oxopyrrolidin-1-yl)propyl]pyrazine-2-carboxamide;
3-Amino-6-bromo-N-(cyanomethyl)pyrazine-2-carboxamide;
Methyl 3-amino-6-[4-(pyrrolidin-1-ylsulfonyl)phenyl]pyrazine-2-carboxylate;
Methyl 3-{[2,6-dimethoxy-4-(2-phenylethoxy)benzyl]amino}-6-[4-(pyrrolidin-1-ylsulfonyl)phenyl]pyrazine-2-carboxylate polystyrene;
3-{[2,6-Dimethoxy-4-(2-phenylethoxy)benzyl]amino}-6-[4-(pyrrolidin-1-ylsulfonyl)phenyl]pyrazine-2-carboxylic acid polystyrene;

as a free base or a salt, solvate or solvate of a salt thereof.

Listed below are definitions of various terms used in the specification and claims to describe the present invention.

For the avoidance of doubt it is to be understood that where in this specification a group is qualified by 'hereinbefore defined', 'defined hereinbefore', 'is as defined above' or 'are as defined above' the said group encompasses the first occurring and broadest definition as well as each and all of the preferred definitions for that group.

For the avoidance of doubt it is to be understood that in this specification 'C$_{0-6}$' means a carbon group having 0, 1, 2, 3, 4, 5 or 6 carbon atoms.

The term "alkyl" as used herein includes both straight and branched chain alkyl groups. C$_{1-6}$alkyl may be methyl, ethyl, n-propyl, i-propyl, n-butyl, i-butyl, s-butyl, t-butyl, n-pentyl, i-pentyl, t-pentyl, neo-pentyl, hexyl.

The term "C$_{3-6}$ cycloalkyl" as used herein refers to a monocyclic hydrocarbon ring system having 3 to 6 carbon atoms. C$_{3-6}$ cycloalkyl amy be cyclopropyl, cyclobutyl, cyclopentyl, cyclohexyl.

The term "alkoxy" as used herein, unless stated otherwise includes "alkyl" O groups in which "alkyl" is as hereinbefore defined. C$_{1-6}$alkoxy may be methoxy, ethoxy, n-propoxy, i-propoxy, n-butoxy, i-butoxy, s-butoxy, t-butoxy, n-pentyloxy, i-pentyloxy, t-pentyloxy, neo-pentyloxy, hexyloxy.

The term "alkenyl" as used herein includes both straight and branched chain alkenyl groups but references to individual alkenyl groups such as 2-butenyl is specific for the straight chain version only. $C_{2-6}$ alkenyl may be, but are not limited to, vinyl, allyl, propenyl, i-propenyl, butenyl, i-butenyl, crotyl, pentenyl, i-pentenyl or hexenyl.

The term "alknyl" as used herein includes both straight and branched chain alkynyl groups but references to individual alkynyl groups such as 2-butynyl are specific for the straight chain version only. $C_{2-6}$ alkynyl may be, but are not limited to, ethynyl, propargyl, butynyl, i-butynyl, pentynyl, i-pentynyl or hexynyl.

In this specification, unless stated otherwise, the terms "aryl" refers to an optionally substituted monocyclic or bicyclic hydrocarbon ring system containing at least one aromatic ring. The "aryl" may be fused with a $C_{5-7}$cycloalkyl ring to form a bicyclic hydrocarbon ring system. Examples and suitable values of the term "aryl" are phenyl, naphthyl, indanyl or tetralinyl.

In this specification, unless stated otherwise, the terms "heteroaryl" and "5 or 6 membered heteroaromatic ring" containing one or more heteroatoms selected from N, O and S may be, but are not limited to, furyl, imidazolyl, isoxazolyl, isothiazolyl, oxazolyl, pyrazinyl, pyrazolyl, pyridazinyl, pyridyl, pyrimidyl, pyrrolyl, thiazolyl or thienyl.

In this specification, unless stated otherwise, the term "5 or 6 membered, saturated, partly saturated or unsaturated ring containing atoms independently selected from C, N, O or S" may be, but are not limited to, furyl, isoxazolyl, isothiazolyl, oxazolyl, pyrazinyl, pyrazolyl, pyridazinyl, pyridyl, pyrimidyl, pyrrolyl, thiazolyl, thienyl, imidazolyl, imidazolidinyl, imidazolinyl, morpholinyl, piperazinyl, piperidyl, piperidonyl, pyrazolidinyl, pyrazolinyl, pyrrolidinyl, pyrrolinyl, tetrahydropyranyl, thiomorpholinyl, cyclohexyl or cyclopentyl.

In this specification, unless stated otherwise, the term "5 or 6 membered heteroaromatic ring containing one or more heteroatoms independently selected from N, O, or S" may be, but are not limited to, furyl, isoxazolyl, isothiazolyl, oxazolyl, pyrazinyl, pyrazolyl, pyridazinyl, pyridyl, pyrimidyl, pyrrolyl, thiazolyl, thienyl or imidazolyl.

In this specification, unless stated otherwise, the term "5 or 6 membered heterocyclic ring containing one or more heteroatoms independently selected from N, O, or S" may be, but are not limited to, imidazolidinyl, imidazolinyl, morpholinyl, piperazinyl, piperidyl, piperidonyl, pyrazolidinyl, pyrazolinyl, pyrrolidinyl, pyrrolinyl, tetrahydropyranyl or thiomorpholinyl.

In this specification, unless stated otherwise, the term halogen may be fluorine, chlorine, bromine or iodine. The term Hal in the formulas means halogen.

The present invention relates to the use of compounds of formula I as hereinbefore defined as well as to the salts, solvates and solvates of salts thereof. Salts for use in pharmaceutical compositions will be pharmaceutically acceptable salts, but other salts may be useful in the production of the compounds of formula I.

Both organic and inorganic acids can be employed to form non-toxic pharmaceutically acceptable acid addition salts of the compounds, e.g. hydrochlorides, of this invention. In addition, a suitable pharmaceutically acceptable salt of the compounds of the invention, which is sufficiently acidic is an alkali metal salt, an alkaline earth metal salt or a salt with an organic base, which affords a physiologically-acceptable cation.

It will be understood that certain compounds of the present invention may exist in solvated, for example hydrated, as well as unsolvated forms. It is to be understood that the present invention encompasses all such solvated forms which possess the above-mentioned activity.

Some compounds of formula I may have chiral centres and/or geometric isomeric centres (E- and Z-isomers), and it is to be understood that the invention encompasses all such optical, diastereoisomers and geometric isomers that possess GSK3 inhibitory activity.

It is to be understood that the present invention relates to any and all tautomeric forms of the compounds of formula I.

An object of the invention is to provide compounds of formula I for therapeutic use, especially compounds that are useful for the prevention and/or treatment of conditions associated with glycogen synthase kinase-3 (GSK3) in mammals including man. Particularly, compounds of formula I exhibiting a selective affinity for GSK-3.

Methods of Preparation

Another aspect of the present invention provides a process for preparing a compound of formula I as a free base or a pharmaceutically acceptable salt, solvate or solvate of a salt thereof.

Throughout the following description of such processes it is understood that, where appropriate, suitable protecting groups will be added to, and subsequently removed from, the various reactants and intermediates in a manner that will be readily understood by one skilled in the art of organic synthesis. Conventional procedures for using such protecting groups as well as examples of suitable protecting groups are described, for example, in "Protective Groups in Organic Synthesis" T. W. Green, P. G. M. Wuts, Wiley-Interscience, New York, 1999.

Methods of Preparation of the Intermediates

The process for the preparation of the intermediates, wherein Y, X, Z, P, Q, R, $R^1$, $R^2$, $R^3$, $R^4$, $R^5$, $R^6$, $R^7$, $R^8$, $R^9$, $R^{10}$, $R^{11}$, $R^{12}$, A, m and n are, unless specified otherwise, defined as in formula I, comprises of:

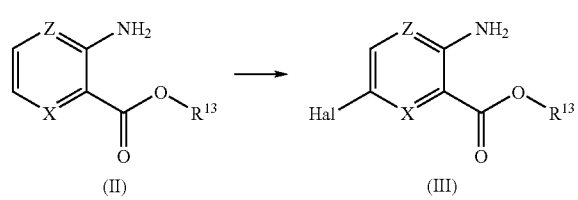

(i) halogenation of a compound of formula II, wherein Z is N and X are N or CH, Hal is halogen, $R^{13}$ is hydrogen, $C_{1-6}$alkyl or when $R^{13}$ is hydrogen in the form of a salt such as a sodium salt, to obtain a compound of formula III, may be carried out using a suitable halogenating reagent such as iodine, bromine, chlorine, halide salts e.g. ICl, BrCl or HOCl or other suitable halogenation reagents such as N-bromosuccinimide or phosphorous tribromide. The reaction may be catalysed by metals or acids such as Fe, Cu-salts, acetic acid or sulfuric acid or aided by oxidising agents such as nitric acid, hydrogen peroxide or sulfur trioxide. The reaction may be carried out in a suitable solvent such as water, acetic acid or chloroform at a temperature in the range of −70° C. to +100° C.

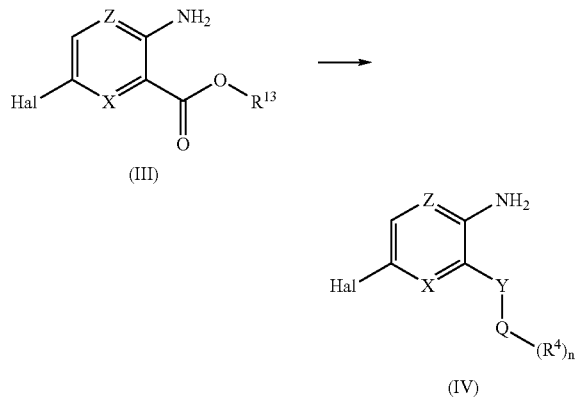

(III)

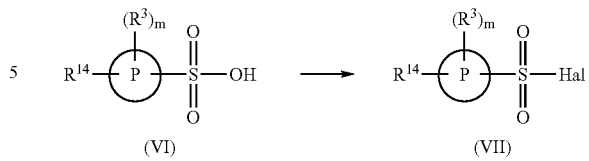

(VI) → (VII)

(iv) halogenating a compound of formula VI, wherein $R^{14}$ is halogen e.g. bromine or chlorine or $CH_3(CO)NH$ and P, $R^3$ and m are as defined above, to obtain a compound of formula VII may be carried out by treatment of a compound of formula VI with a halogenation reagents such as thionyl chloride or oxalyl chloride. The reaction may be performed neat or in a suitable solvent such as tetrahydrofuran, dioxane, N,N-dimethylformamide or methylene chloride at a temperature range between −20° C. and +60° C.;

(IV)

(ii) amidation of a compound of formula III, wherein Z is N and X are N, Hal is halogen, $R^{13}$ is $C_{1-6}$alkyl to obtain a compound of formula IV, wherein Y is $CONR^5$ and Q, $R^4$ and n are as defined above, may be carried out by treating a compound of formula III with the appropriate amine such as a compound of formula V wherein Q, $R^4$, $R^5$ and n are as defined above. The reaction may be performed neat or using a suitable solvent such as N,N-dimethylformamide, methylene chloride or ethyl acetate at a temperature ranging from −25° C. to +150° C. The reaction may be aided by using a base such as potassium carbonate, trietylamine or 1,8-diazabicyclo[5.4.0]undec-7-ene or an acid such as trimethylaluminum or p-toulenesulfonic acid.

(VIII)

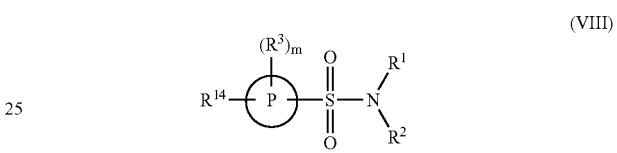

(v) amidation of a compound of formula VII, wherein $R^{14}$ is halogen e.g. bromine or chlorine or $CH_3(CO)NH$, Hal is fluorine, chlorine or bromine and P, $R^3$ and m are as defined above, to obtain a compound of formula VIII, wherein $R^{14}$ is bromine or $CH_3(CO)NH$ and P, $R^1$, $R^2$, $R^3$ and n are as defined above, may be carried out by reacting a compound of formula VII with the suitable amine $HNR^1R^2$. The reaction may be performed in a suitable solvent such as tetrahydrofuran, dioxane, N,N-dimethylformamide or methylene chloride in a temperature range between 0° C. and +50° C.

(V)

(iii) amidation of a compound of formula III, wherein $R^{13}$ is hydrogen, to obtain a compound of formula IV, wherein Y is $CONR^5$ and $R^4$ is a substituents that is not is susceptible to certain coupling agents, may be performed by activation of a compound of formula III by treating the compound with coupling reagents such as 1,3-diisopropylcarbodiimide, 1-[3-(dimethylamino)propyl]-3-ethylcarbodiimide hydrochloride, 1,3-dicyclohexylcarbodiimide, O-(benzotriazol-1-yl)-N,N,N',N'-tetramethyluronium tetrafluoroborate, O-(benzotriazol-1-yl)-N,N,N',N'-tetramethyluronium hexafluorophosphate, 1,1'-carbonyldiimidazole or O-(7-azabenzotriazol-1-yl)-N,N,N',N'-tetramethyluronium hexafluorophosphate where the reaction may be aided by the addition of 1-hydroxybenzotriazole hydrate, or using an acyl halide reagent such as cyanuric chloride, oxalyl chloride, thionyl chloride or bromotrispyrrolidinophosphonium hexafluorophosphate, followed by treatment with the appropriate amine such as a compound of formula V wherein Q, $R^4$, $R^5$, and n are as defined above, in a suitable solvent such as methylene chloride chloroform, acetonitrile or tetrahydrofuran and at a rection temperature between 0° C. and reflux. The reaction may be aided by using a base such as potassium carbonate or a trialkyl amine e.g triethyl amine or N-ethyl-N,N-diisopropyl amine.

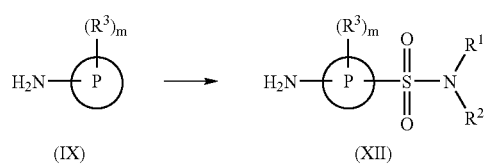

(IX) → (XII)

(vi) conversion of a compound of formula IX, wherein P, $R^3$ and m are as defined above, to obtain a compound of formula XII, wherein P, $R^1$, $R^2$, $R^3$ and n are as defined above, may be carried out by treating a compound of formula IX with a sulfonating reagent such as chloro sulfonic acid followed by addition of a suitable amine, $HNR^1R^2$. The reaction may be performed neat or in an appropriate solvent such as tetrahydrofuran or methylene chloride and at a reaction temperature between +25° C. and reflux.

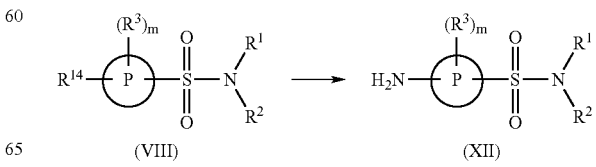

(VIII) → (XII)

(vii) transformation of a compound of formula VIII, wherein $R^{14}$ is $CH_3(CO)NH$, and $R^1$, $R^2$, $R^3$, m and P are as defined above, to a compound of formula XII may be carried out by the reaction with an acid such as hydrochloric acid or hydrobromic acid at a temperature range between +25° C. and +110° C.

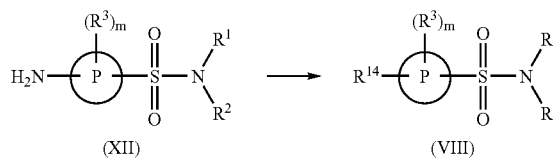

(viii) conversion of a compound of formula XII to obtain a compound of formula VIII, wherein $R^{14}$ is bromine, $R^1$, $R^2$, $R^3$, m and P are as defined above, may be carried out by treatment of a compound of formula XII with sodium nitrite and hydrobromic acid followed by the addition of a bromide source such as CuBr in an appropriate solvent such as water at a temperature range between 0° C. and +5° C.

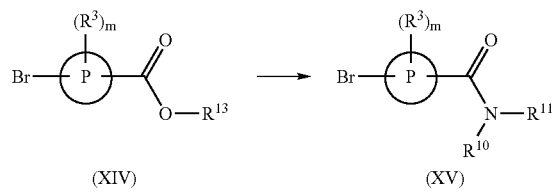

(ix) formation of an amide of formula XV, wherein $R^{10}$, $R^{11}$, $R^3$, m and P are as defined above, may be carried out by treating a compound of formula XIV, wherein $R^{13}$ is $C_{1-6}$alkyl, with the appropriate amine $HNR^{10}R^{11}$. The reaction may be performed neat or using a suitable solvent such as N,N-dimethylformamide, methylene chloride or ethyl acetate at a temperature ranging from −25° C. to +150° C. The reaction may be aided by using a base such as potassium carbonate, trietyl amine or 1,8-diazabicyclo[5.4.0]undec-7-ene or an acid such as trimethylaluminum or p-toulenesulfonic acid.

(x) amidation of a compound of formula XIV, wherein $R^{13}$ is hydrogen and $R^3$, m and P are as defined above to obtain a compound of formula XV may be performed by activation of a compound of formula XIV by treating the compound with coupling reagents such as 1,3-diisopropylcarbodiimide, 1-[3-(dimethylamino)propyl]-3-ethylcarbodiimide hydrochloride, 1,3-dicyclohexylcarbodiimide, O-(benzotriazol-1-yl)-N,N,N',N'-tetramethyluronium tetrafluoroborate, O-(benzotriazol-1-yl)-N,N,N',N'-tetramethyluronium hexafluorophosphate, 1,1'-carbonyldiimidazole or O-(7-azabenzotriazol-1-yl)-N,N,N',N'-tetramethyluronium hexafluorophosphate where the reaction may be aided by the addition of 1-hydroxybenzotriazole hydrate, or using an acyl halide reagent such as cyanuric chloride, oxalyl chloride, thionyl chloride or bromotrispyrrolidinophosphonium hexafluorophosphate, followed by treatment with the appropriate amine $HNR^{10}R^{11}$. The reaction may be carried out in a suitable solvent such as N,N-dimethylformamide, acetonotrile or methylene chloride at a temperature ranging from −25° C. to +150° C., with or without a suitable base such as an alkyl amine e.g. triethyl amine, N-ethyl-N,N-diisopropyl amine or N-methyl morpholine, or potassium carbonate or sodium hydroxide.

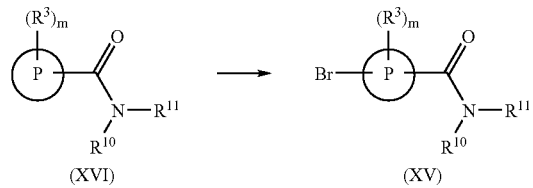

(xi) bromination of a compound of formula XVI to obtain a compound of formula XV, wherein $R^{10}$, $R^{11}$, $R^3$, m and P are as defined above, may be carried out by treatment of a compound of formula XVI with bromine with or without an appropriate base such as sodium acetate in a suitable solvent such as acetic acid.

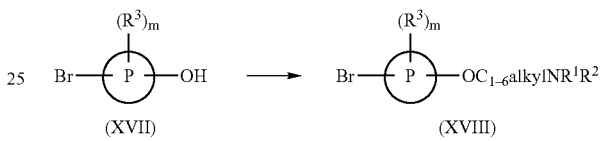

(xii) conversion of a compound of formula XVII, wherein $R^3$, m and P are as defined above, to obtain a compound of formula XVIII, wherein $R^1$, $R^2$, $R^3$, m, $C_{1-6}$alkyl and P are as defined above, may be carried out by reacting a compound of formula XVII with a suitable alcohol, $R^1R^2NC_{1-6}$alkylOH in the presence of triphenylphosphine and an appropriate azidodicarboxylate such as diethyl azidodicarboxylate. The reaction may be performed in a suitable solvent such as tetrahydrofuran, toluene or methylene chloride and at a reaction temperature between 0° C. to +60° C.

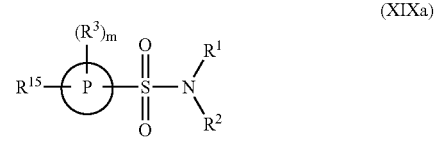

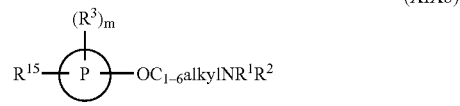

(xiii) borylation of a compounds of formula VIII wherein $R^{14}$ is halogen e.g. bromine, XV and XVIII to obtain compounds of formula XIXa-c (XIXa from VIII, XIXb from XVIII and XIXc from XV), wherein $R^{15}$, $R^1$, $R^2$, $R^3$, $R^{10}$, $R^{11}$, m, $C_{1-6}$alkyl and P are as defined above and $R^{15}$ may be a group outlined in Scheme I, wherein B is boron, $R^{16}$ and $R^{17}$ are $C_{1-6}$alkoxy or hydroxy, or $C_{1-3}$alkoxy fused together to form a 5 or 6 membered cyclic boron-oxygen-$C_{2-3}$alkyl species and the alkoxy, the aryl group or 5 or 6 membered cyclic boron-oxygen-$C_{2-3}$alkyl species may be optionally substituted, may be carried out by a reaction with:

a) butyllithium or magnesium and a suitable boron compound such as trimethyl borate or triisopropyl borate. The reaction may be performed in a suitable solvent such as tetrahydrofuran, hexane or methylene chloride in a temperature range between −78° C. and +20° C.; or, b) a palladium catalyst such as palladium tetrakis(triphenylphosphine), palladium diphenylphosphineferrocene dichloride or palladium acetate with or without a suitable ligand such as 2-(dicyclohexylphosphino)biphenyl, and a suitable boron species such as bis(catecholato)diboron, bis(pinacolato)diboron or pinacolborane. A suitable base, which under the reaction conditions do not promote dimerisation of compounds of formula XIXa-c, such as a tertiary amine such as trietyl amine or diisopropylethyl amine or potassium acetate may be used. The reaction may be performed in a solvent such as dioxane, toluene or acetonitrile at temperatures between +80° C. and +100° C.

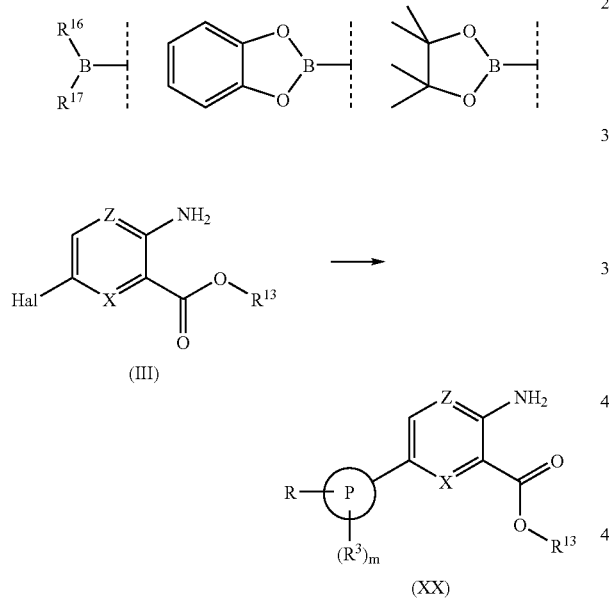

(xiv) conversion of a compound of formula III to a compound of formula XX, wherein, $R^{13}$ is $C_{1-6}$alkyl and X, Z, R, $R^3$, P and m are as defined above, may be carried out by a de-halogen coupling with a suitable compound of formula XIXa-c.

The reaction may be carried out by coupling of a compound of formula III with an appropriate aryl boronic acid or a boronic ester of formula XIXa-c (the boronic acid or boronic ester may be formed in situ using the compounds of formula VIII wherein $R^{14}$ is halogen e.g. bromine, XV and XVIII and conditions described in (xiii)). The reaction may be carried out using a suitable palladium catalyst such as Pd(PPh$_3$)$_4$, Pd(dppf)Cl$_2$ or Pd(OAc)$_2$ with or without a suitable ligand such as P(tert-butyl)$_3$ or 2-(dicyclohexylphosphino)biphenyl or a nickel catalyst such as nickel on charcoal or Ni(dppe)Cl$_2$ together with Zn and sodium triphenylphosphinetrimetasulfonate. A suitable base such as an alkyl amine e.g. triethyl amine, or potassium carbonate, sodium carbonate, sodium hydroxide or cesium fluoride may be used in the reaction, which is performed in a temperature range between +20° C. and +160° C. using an oil bath or a microwave oven in a suitable solvent or solvent mixture such as toluene, tetrahydrofuran, dimethoxyethane/water or N,N-dimethylformamide.

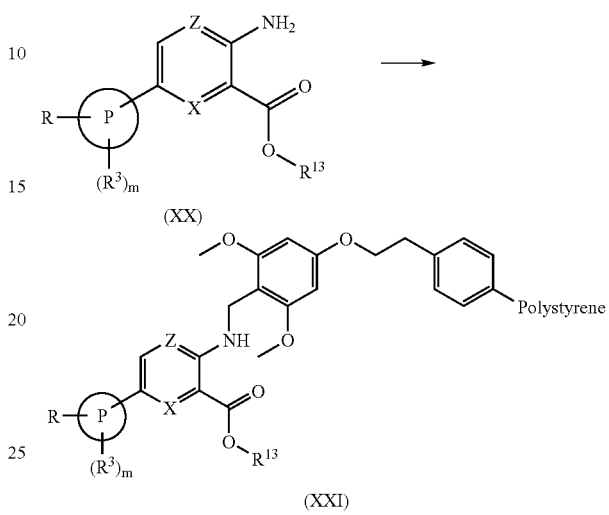

(xv) conversion of a compound of formula XX, wherein $R^{13}$ is $C_{1-6}$alkyl and R, $R^3$, X, Z and m are as defined above, to a compound of formula XXI may be carried out by reaction with a suitable solid phase reagent such as a formyl polystyrene e.g. 2-(3,5-dimethoxy-4-formylphenoxy)ethyl polystyrene or 2-(4-formyl-3-methoxyphenoxy)ethyl polystyrene in a suitable solvents such as N,N-dimethylformamide or methylene chloride in the presence of a suitable acid e.g. acetic acid and a suitable reducing reagent such as sodiumtriacetoxy borohydride or sodium cyanoborohydride at a suitable reaction temperature ranging between 0° C. and +50° C. The reaction may be aided be the presence of trimethylsilyl chloride.

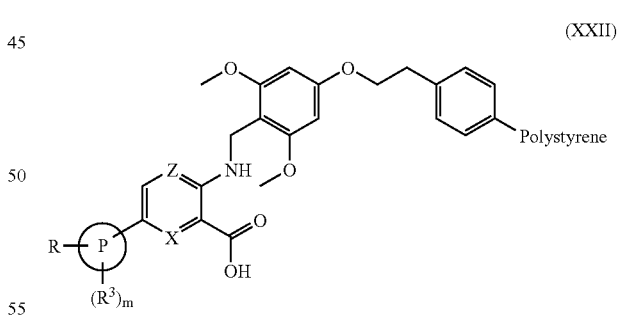

(xvi) hydrolysis of a compound of formula XXI, wherein R, $R^3$, X, Z and m are as defined above, to a compound of formula XXII may be carried out in a suitable solvent such as water, tetrahydrofuran or mixtures thereof in the presence of a suitable base such as sodium hydroxide, potassium hydroxide or lithium hydroxide at a suitable reaction temperature ranging between +25° C. and reflux.

Methods of Preparation of End Products

Another object of the invention are processes for the preparation of a compound of general formula I, wherein Y, X, Z, P, Q, R, R$^1$, R$^2$, R$^3$, R$^4$, R$^5$, R$^6$, R$^7$, R$^8$, R$^9$, R$^{10}$, R$^{11}$, R$^{12}$, A, m and n are, unless specified otherwise, defined as in formula I, comprising of:

A

De-halogen coupling, wherein R$^3$ and R$^4$ are substituents that are not susceptible to certain agents in the reaction, of a compound of formula IV with a appropriate aryl species to give a compound of formula I:

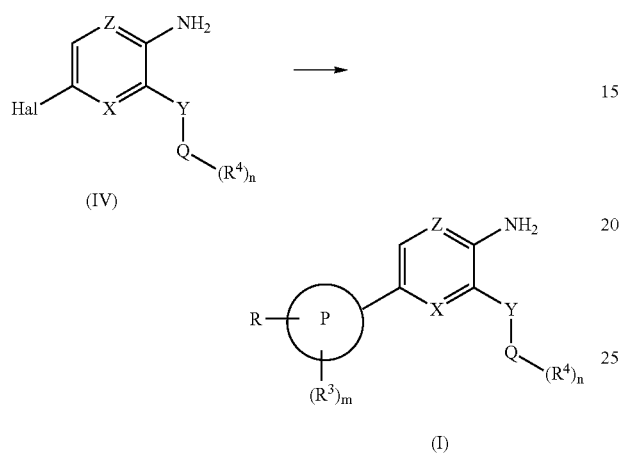

Thus, the de-halogen coupling according to process A may be carried out by coupling of a compound of formula IV with:

a) an appropriate aryl halogen such as aryl iodide, aryl bromide or aryl chloride in the presence of metals such as copper, nickel or zinc and nickel complexes, copper oxide or palladium acetate and tetrabutylammonium bromide and a base such as potassium carbonate or trietylamine. The reaction may occur at a temperature between 20° C. and 180° C. in a suitable solvent such as N,N-dimetylformamide, toluene or 2-pentanol; or, b) an appropriate aryl boronic acid or a bornic ester such as compounds of formula XIXa-c (the boronic acid or boronic ester may be formed in situ using the compounds of formula VIII wherein R$^{14}$ is halogen e.g. bromine, XV and XVIII and conditions described in (xiii)). The reaction may be carried out using a suitable palladium catalyst such as Pd(PPh$_3$)$_4$, Pd(dppf)Cl$_2$ or Pd(OAc)$_2$ with or wiyhout a suitable ligand such as P(tert-butyl)$_3$ or 2-(dicyclohexylphosphino)biphenyl or a nickel catalyst such as nickel on charcoal or Ni(dppe)Cl$_2$ together with Zn and sodium triphenylphosphinetrimetasulfonate. A suitable base such as an alkyl amine e.g. triethyl amine, or potassium carbonate, sodium carbonate, sodium hydroxide or cesium fluoride may be used in the reaction, which is performed in the temperature range between +20° C. and +160° C. using an oil bath or in a microwave oven in a suitable solvent or solvent mixture such as toluene, tetrahydrofuran, dimethoxyethane/water or N,N-dimethylformamide; or, c) an appropriate aryl stannane in the presence of palladium catalyst such as Pd(PPh$_3$)$_4$, Pd(PPh$_3$)$_2$Cl$_2$ or Pd(dba)$_3$ and if needed a helping reagent such as 4-tert-butylcatechole, lithium chloride or potassium carbonate. Suitable solvents may be toluene, tetrahydrofuran or N,N-dimethylformamide.

The reaction may occur in a temperature range of +20° C. and +120° C.

B

Amidation, wherein R$^3$ and R$^4$ are substituents that are not susceptible to certain agents in the reaction, of a compound of formula XXII with the appropriate amine:

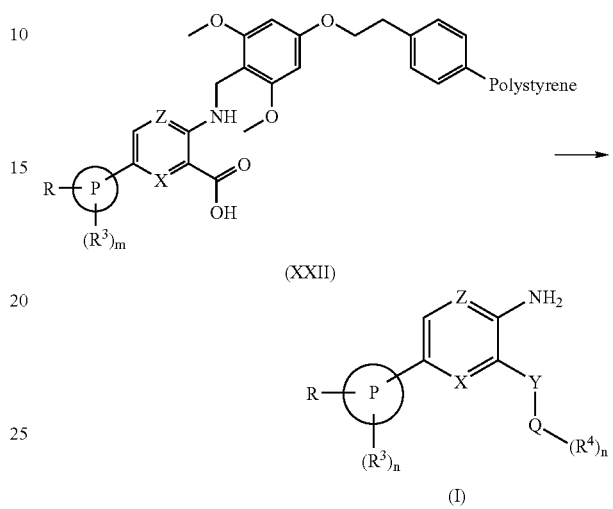

Thus, the amidation of a compound of formula XXII, may be performed by activation of a compound of formula XXII by treating the compound with coupling reagents such as 1,3-diisopropylcarbodiimide, 1-[3-(dimethylamino)propyl]-3-ethylcarbodiimide hydrochloride, 1,3-dicyclohexylcarbodiimide, O-(benzotriazol-1-yl)-N,N,N',N'-tetramethyluronium tetrafluoroborate, O-(benzotriazol-1-yl)-N,N,N',N'-tetramethyluronium hexafluorophosphate, 1,1'-carbonyldiimidazole or O-(7-azabenzotriazol-1-yl)-N,N,N', N'-tetramethyluronium hexafluorophosphate where the reaction may be aided by the addition of 1-hydroxybenzotriazole hydrate, or using an acyl halide reagent such as cyanuric chloride, oxalyl chloride, thionyl chloride or bromotrispyrrolidinophosphonium hexafluorophosphate followed by treatment with the appropriate amine such as a compound of formula V followed by, cleavage of the solid phase moiety by treatment with an suitable acid such as trifluoroacetic acid in a suitable solvent such as methylene chloride or chloroform and at a reaction temperature between 0° C. and reflux to give the compound of formula (I).

The hydrochloric salt of compound of formula I may be obtained from a compound of formula I by treatment with hydrochloric acid at a temperature range between 0° C. and +25° C., in suitable solvent such as methylene chloride, tetrahydrofuran, diethyl ether or methylene chloride/methanol mixture.

WORKING EXAMPLES

Example 1

1-[(4-Bromophenyl)sulfonyl]pyrrolidine

Pyrrolidine (2.5 g, 35.2 mmol) was added to a solution of 4-bromobenzenesulfonyl chloride (4.5 g, 17.6 mmol) in methylene chloride (10 mL) at 0° C. The mixture was stirred for 2 h and an aqueous sodium hydroxide solution (1 M, 5 mL) was added and stirring was continued for another 10 min. The organic phase was separated and diluted with methylene chloride (40 mL), washed with aqueous HCl (1 M, 10 mL), and water (2×10 mL). The organic phase was dried (sodium sulphate) and the solvent was evaporated. The title compound was isolated in 5.0 g (98% yield) as a white solid: $^1$H NMR (CDCl$_3$, 400 MHz) δ 7.65 (m, 4H), 3.20 (m, 4H), 1.74 (m, 4H); $^{13}$C NMR (CDCl$_3$, 100 MHz) δ 135.93, 132.17, 128.84, 127.39, 47.84, 25.13; MS (ES) m/z 290 and 292 (M$^+$+1).

Example 2

4-(Pyrrolidin-1-ylsulfonyl)phenylboronic acid n-Butyllithium (20 mL, 31 mmol) was added dropwise over 30 min to a cooled (−78° C.) solution of 1-[(4-bromobenzenesulfonyl)pyrrolidine (3.0 g, 10.3 mmol) and triisopropyl borate (7.2 mL, 30.9 mol) in anhydrous tetrahydrofuran (10 mL) under a nitrogen atmosphere. The reaction mixture was stirred for 1 h at −78° C. whereafter the temperature was allowed to reach room temperature over 3 h. Silica gel was added and the solvent was evaporated. Chromatography on a silica gel column using a gradient methylene chloride (100%) to methylene chloride/ethanol, (1:1), gave 1.85 g (70% yield) of the title compound as a white solid: $^1$H NMR (CD$_3$OD, 400 MHz) δ 7.90 (d, J=7 Hz, 2H), 7.75 (d, J=8 Hz, 2H), 3.21 (m, 4H), 1.72 (m, 4H); $^{13}$C NMR (CDCl$_3$/CD$_3$OD (1:1), 100 MHz) δ 136.79, 133.50, 125.48, 47.19, 24.30; MS (ES) m/z 256 (M$^+$+1).

Example 3

4-[(4-Methylpiperazin-1-yl)sulfonyl]phenylboronic acid

Triisopropyl borate (0.64 mL, 2.8 mmol) was added to a solution of 1-[(4-bromophenyl)sulfonyl]-4-methylpiperazine (0.602 g, 1.9 mmol; described: in Keasling, H. H. et el. *J. Med. Chem.* 1965, 8, 548-550) in anhydrous tetrahydrofuran (7 mL) at −78° C. under a nitrogen atmosphere followed by dropwise addition of n-butyllithium (1.4 mL, 2.2 mmol). The resulting mixture was stirred at −78° C. for 2 h and at room temperature for another 16 h. Water (2.0 mL) was added and the mixture stirred for 30 min and evaporated to dryness. The residue was pre-adsorbed onto silica and purified by column chromatography on silica using methylene chloride/methanol, (9:1 to 1:9), as the eluent. The product was re-crystallized from water to give 311 mg (58% yield) of the title compound as white crystals: mp 215-218° C.; $^1$H NMR (DMSO-d$_6$, 400 MHz) δ 8.47 (br s, 2H), 8.05 (d, J=8 Hz, 2H), 7.73 (d, J=8 Hz, 2H), 3.77 (m, 2H), 3.40 (m, 2H), 3.13 (m, 2H), 2.71 (s, 3H), 2.65 (m, 2H); $^{13}$C NMR (DMSO-d$_6$, 100 MHz) δ 133.7, 133.3, 124.7, 49.8, 41.6, 41.4; MS (TSP) m/z 285 (M$^+$+1).

Example 4

3-Amino-6-bromo-N-(2-morpholin-4-ylethyl)pyrazine-2-carboxamide 1-(3-Dimethylaminopropyl)-3-ethylcarbodiimide hydrochloride (0.68 g, 3.5 mmol) was added in one portion to a stirred suspension of 2-morpholin-4-ylethanamine (0.422 g, 3.2 mmol), 3-amino-6-bromopyrazine-2-carboxylic acid (0.64 g, 3.0 mmol; described in: Ellingson, R. C.; Henry, R. L. *J. Am. Chem. Soc.* 1949, 2798-2800), and 1-hydroxybenzotriazole hydrate (0.48 g, 3.5 mmol) in acetonitrile (25 mL) at 0° C. The cooling bath was removed and stirring was continued at room temperature for 7 h. The solid was filtered off, washed with acetonitrile and purified by column chromatography on silica using methylene chloride/methanol/triethyl amine, (95:5:0.1), to give 0.68 g (69% yield) of the title compound: $^1$H NMR (DMSO-d$_6$, 400 MHz) δ 8.53 (m, 1H), 8.34 (s, 1H), 8.68 (br s, 2H), 3.57 (t, J=5 Hz, 4H), 3.37 (q, J=7 Hz, 2H), 2.47 (q, J=7 Hz, 2H), 2.40 (m, 4H); MS (ES) m/z 330 and 332 (M$^+$+1).

Example 5

3-Amino-6-bromo-N-[2-(1H-imidazol-4-yl)ethyl]pyrazine-2-carboxamide

The title compound was prepared as described for Example 4 using histamine. Yield: 18%: $^1$H NMR (DMSO-d$_6$, 400 MHz) δ 11.87 (br s, 1H), 8.80 (m, 1H), 8.34 (s, 1H), 7.72 (br s, 2H), 7.55 (s, 1H), 6.83 (s, 1H), 3.49 (q, J=7 Hz, 2H), 2.75 (t, J=7 Hz, 2H); MS (ES) m/z 311 and 313 (M$^+$+1).

Example 6

3-Amino-6-bromo-N-[3-(1H-imidazol-1-yl)propyl]pyrazine-2-carboxamide

The title compound was prepared as described for Example 4 using 3-(1H-imidazol-1-yl)propan-1-amine. Yield: 67%: $^1$H NMR (DMSO-d$_6$, 400 MHz) δ 8.72 (m, 1H), 8.34 (s, 1H), 7.71 (br s, 2H), 7.65 (s, 1H), 7.20 (s, 1H), 6.88 (s, 1H), 3.98 (t, J=7 Hz, 2H), 3.24 (q, J=6 Hz, 2H), 1.95 (quin, J=7 Hz, 2H); MS (ES) m/z 325 and 327 (M$^+$+1).

Example 7

3-Amino-6-bromo-N-(2-thien-2-ylethyl)pyrazine-2-carboxamide

A solution of 3-amino-6-bromopyrazine-2-carboxylic acid (0.50 g, 2.3 mmol; described in: Ellingson, R. C.; Henry, R. L. *J. Am. Chem. Soc.* 1949, 2798-2800), 1-hydroxybenzotriazole hydrate (0.41 g, 2.7 mmol) in acetonitrile (5 mL) were added to a stirred solution of 2-thien-2-ylethanamine (0.32 g, 2.5 mmol) in acetonitrile (5 mL) followed by addition of 1-(3-dimethylaminopropyl)-3-ethylcarbodiimide hydrochloride (0.52 g, 2.7 mmol) and acetonitrile (1.5 mL). The resulting mixture was stirred at room temperature over night and the solvent was evaporated. The residue was re-crystallized from acetonitrile and subsequently from methanol to give 0.5 g (66% yield) of the title compound: $^1$H NMR DMSO-d$_6$, 400 MHz) δ 8.73 (t, J=6 Hz, 1H), 8.34 (s, 1H), 7.71 (br s, 2H), 7.34 (dd, J=5, 1 Hz, 1H), 6.95 (d, J=3 Hz, 1H), 6.91 (m, 1H), 3.50 (q, J=7 Hz, 2H), 3.05 (t, J=7 Hz, 2H); MS (ES) m/z 327 and 329 (M$^+$+1).

The following Examples, 8-12, were synthesized as described for Example 7.

Example 8

3-Amino-6-bromo-N-(thien-2-ylmethyl)pyrazine-2-carboxamide

Starting material: 1-thien-2-ylmethanamine. Purification by re-crystallization from methanol gave the title compound. Yield: 73%: $^1$H NMR (DMSO-d$_6$, 400 MHz) δ 9.20 (t, J=6 Hz, 1H), 8.35 (s, 1H), 7.72 (br s, 2H), 7.37 (dd, J=5, 1 Hz, 1H), 7.01 (dd, J=3, 1 Hz, 1H), 6.95 (dd, J=5, 3 Hz, 1H), 4.59 (d, J=6 Hz, 2H); MS (ES) m/z 313 and 315 (M$^+$+1).

Example 9

3-Amino-6-bromo-N-(2-methoxyethyl)pyrazine-2-carboxamide

Starting material: 2-methoxyethylamine. Purification by re-crystallization from methanol gave the title compound. Yield: 77%: $^1$H NMR (DMSO-d$_6$, 400 MHz) δ 8.51 (s, 1H), 8.36 (s, 1H), 7.73 (br s, 2H), 3.45 (s, 4H), 3.27 (s, 3H); MS (ES) m/z 275 and 277 (M$^+$+1).

Example 10

3-Amino-6-bromo-N-(3-methoxypropyl)pyrazine-2-carboxamide

Starting material: 2-methoxypropylamine. Purification by re-crystallization from methanol gave the title compound. Yield: 42%: $^1$H NMR (DMSO-d$_6$, 400 MHz) δ; 8.64 (m, 1H), 8.33 (s, 1H), 7.70 (br s, 2H), 3.37 (t, J=6 Hz, 2H), 3.31 (t, J=7 Hz, 2H), 3.24 (s, 3H), 1.75 (quin, J=7 Hz, 2H); MS (ES) m/z 289 and 291 (M$^+$+1).

Example 11

3-Amino-6-bromo-N-[3-(2-oxopyrrolidin-1-yl)propyl]pyrazine-2-carboxamide

Starting material: 1-(3-aminopropyl)-2-pyrrolidinone. Purification by column chromatography on silica using methylene chloride/methanol/triethyl amine, (98:2:0.1), gave the title compound. Yield: 89%: $^1$H NMR (DMSO-d$_6$, 400 MHz) δ 8.65 (s, 1H), 8.36 (s, 1H), 7.73 (br s, 2H), 3.36 (m, 2H), 3.22 (m, 4H), 2.23 (m, 2H), 1.93 (m, 2H), 1.70 (m, 2H); MS (ES) m/z 342 and 344 (M$^+$+1).

Example 12

3-Amino-6-bromo-N-(cyanomethyl)pyrazine-2-carboxamide

Starting material: aminoacetonitril. Purification by re-crystallization from methanol gave the title compound. Yield: 47%: $^1$H NMR (DMSO-d$_6$, 400 MHz) δ 9.21 (t, J=6 Hz, 1H), 8.41 (s, 1H), 7.70 (br s, 2H), 4.25 (d, J=6 Hz, 2H).

Example 13

3-Amino-N-(2-morpholin-4-ylethyl)-6-[4-(pyrrolidin-1-ylsulfonyl)phenyl]pyrazine-2-carboxamide hydrochloride n-Butyllithium (1.6 mL, 2.6 mmol) was added dropwise over 10 min to a cooled solution (−78° C.) of triisopropyl borate (0.6 mL, 2.6 mmol), and 1-[(4-bromophenyl)sulfonyl]pyrrolidine (0.251 g, 0.86 mmol) in anhydrous tetrahydrofuran (10 mL) under an atmosphere of nitrogen. The resulting mixture was stirred at −78° C. for 1 h and the mixture was allowed to warm up to room temperature. Aqueous HCl (3 M, 1.4 mL, 4.3 mmol) was added and the mixture was stirred for 10 min followed by the addition of sodium carbonate (0.9 g, 8.6 mmol) and the stirring was continued for another 20 min. 3-Amino-6-bromo-N-(2-morpholin-4-ylethyl)pyrazine-2-carboxamide (0.20 g, 0.61 mmol), and tetrahydrofuran (4 mL) were added followed by addition of Pd(dppf)Cl$_2$ (28 mg, 0.03 mmol) and the resulting mixture was heated at 65° C. for 17 h. The mixture was allowed to return to room temperature and the solvent was evaporated. The resulting residue was suspended in methanol, silica was added, and the solvent was evaporated. Purification by column chromatography on silica using methylene chloride/methanol/triethyl amine, (95:5:0.1), as the eluent gave the free base that was subsequently dissolved in hot methanol and treated with HCl (1 M in diethyl ether). The formed precipitate was filtered off and dried in vacuo to give 72 mg (26% yield) of the title compound as a yellow solid: $^1$H NMR (DMSO-d$_6$, 400 MHz) δ 11.24 (br s, 1H), 9.28 (m, 1H), 8.98 (s, 1H), 8.49 (d, J=8 Hz, 2H), 7.83 (d, J=8 Hz, 2H), 3.97 (m, 2H), 3.87 (d, J=12 Hz, 2H), 3.78 (m, 2H), 3.55 (d, J=12 Hz, 2H), 3.15 (m, 6H), 1.65 (m, 4H); MS (ES) m/z 461 (M$^+$+1).

Example 14

3-Ammo-N-[2-(1H-imidazol-4-yl)ethyl]-6-[4-(pyrrolidin-1-ylsulfonyl)phenyl]pyrazine-2-carboxamide hydrochloride The title compound was prepared as described for Example 13 using 3-amino-6-bromo-N-[2-(1H-imidazol-4-yl)ethyl]pyrazine-2-carboxamide. Purification by preparative HPLC (colonn: C18, 19×100 mm, eluent: water+0.1% TFA/acetonitrile, 50/20 to 50/50) followed by treatment of the base (in methanol) with HCl (1 M in diethyl ether). The formed precipitate was filtered off and dried in vacuo to give the title compound as a yellow solid. Yield: 4%: $^1$H NMR (DMSO-d$_6$, 400 MHz) δ 8.96 (m, 1H), 8.42 (d, J=8 Hz, 2H), 7.87 (d, J=8 Hz, 2H), 7.69 (br s, 2H), 6.97 (br s, 1H), 3.56 (m, 2H), 3.18 (m, 4H), 2.81 (m, 2H), 1.66 (m, 4H); MS (ES) m/z 442 (M$^+$+1).

Example 15

3-Amino-N-[3-(1H-imidazol-1-yl)propyl]-6-[4-(pyrrolidin-1-ylsulfonyl)phenyl]pyrazine-2-carboxamide hydrochloride The title compound was prepared as described for Example 13 using 3-amino-6-bromo-N-[3-(1H-imidazol-1-yl)propyl]pyrazine-2-carboxamide. Purification by column chromatography on silica using methylene chloride/methanol/triethyl amine, (95:5:0.1), gave the free base that was subsequently dissolved in methanol and treated with HCl (1 M in diethyl ether). Additional diethyl ether was added, the formed precipitate was filtered off and dried under vacuo to give the title compound as a yellow solid. Yield: 18%: $^1$H NMR (DMSO-d$_6$, 400) δ 9.21 (s, 1H), 9.06 (m, 1H), 8.96 (s, 1H), 8.43 (d, J=8 Hz, 2H), 7.85 (m, 3H), 7.70 (s, 1H), 4.27 (t, J=7 Hz, 2H), 3.36 (q, J=7 Hz, 2H), 3.17 (m, 4H), 2.14 (quin, J=7 Hz, 2H), 1.65 (m, 4H); MS (ES) m/z 456 (M$^+$+1).

Example 16

3-Amino-6-{4-[(4-methylpiperazin-1-yl)sulfonyl]phenyl}-N-(2-thien-2-ylethyl)pyrazine-2-carboxamide hydrochloride Triisopropyl borate (0.82 mL, 3.6 mmol) was added to a stirred solution of 1-[(4-bromophenyl)sulfonyl]-4-methylpiperazine (0.38 g, 1.2 mmol; described: in Keasling, H. H. et el. *J. Med. Chem.* 1965, 8, 549-550) in anhydrous tetrahydrofuran (115 mL) at −78° C. under an atmosphere of nitrogen, followed by dropwise addition of n-butyllithium (2.4 mL, 3.6 mmol) over 10 min. The resulting mixture was allowed to warm up to room temperature and was stirred for another 10 min at ambient temperature. Aqueous HCl (3 M, 1.9 mL, 6.0 mmol) was added and the mixture was stirred for 10 min, followed by an addition of sodium carbonate (1.26 g, 11.9 mmol). 3-Amino-6-bromo-N-(2-thien-2-ylethyl)pyrazine-2-carboxamide (0.272 g, 0.83 mmol) and Pd(dppf)Cl$_2$ (39 mg, 0.05 mmol) were added and the resulting mixture was heated at 65° C. for 1 h. The solvent was evaporated, the resulting residue dissolved in methylene chloride/water, and the aqueous phase was extracted with ethyl acetate. The combined organic phases were evaporated, methanol was added, and the insoluble material was filtered off. The solvent was evaporated and the residue was purified on a silica gel column using methylene chloride/methanol/triethyl amine, (98:2:0.1), as the eluent. The crude product was purified by re-crystallization from methanol to give the free base that was treated with HCl (1.0 M in diethyl ether, 0.6 mmol). The formed precipitate was filtered off and dried under vacuo to give 25 mg (6% yield) of the title compound as a yellow solid: $^1$H NMR (DMSO-d$_6$, 400 MHz) δ 10.55 (br s, 1H), 9.05 (m, 1H), 8.99 (s, 1H), 8.46 (d, J=8 Hz, 2H), 7.82 (d, J=8 Hz, 2H), 7.37 (d, J=5 Hz, 1H), 6.98 (m, 2H), 3.83 (m, 2H), 3.58 (m, 2H), 3.46 (m, 2H), 3.13 (m, 4H), 2.75 (s, 3H), 2.67 (m, 2H); MS (S) m/z 487 (M$^+$+1).

Example 17

3-Amino-6-{4-[(4-methylpiperazin-1-yl)sulfonyl]phenyl}-N-(thien-2-ylmethyl)pyrazine-2-carboxamide hydrochloride The title compound was prepared as described for Example 16 using 3-amino-6-bromo-N-(thien-2-ylmethyl)pyrazine-2-carboxamide. Yield: 46%: $^1$H NMR (DMSO-d$_6$, 400 MHz) δ 10.9 (br s, 1H), 9.56 (t, J=6 Hz, 1H), 8.99 (s, 1H), 8.48 (d, J=8 Hz, 2H), 7.81 (d, J=8 Hz, 2H), 7.38 (d, J=4 Hz, 1H), 7.05 (s, 1H), 6.97 (dd, J=5, 4 Hz, 1H), 4.68 (d, J=6 Hz, 2H), 3.81 (d, J=12 Hz, 2H), 3.44 (d, J=12 Hz, 2H), 3.15 (m, 4H), 2.72 (s, 3H); MS (ES) m/z 473 (M$^+$+1).

Example 18

3-Amino-N-(2-methoxyethyl)-6-{4-[(4-methylpiperazin-1-yl)sulfonyl]phenyl}pyrazine-2-carboxamide hydrochloride The title compound was prepared as described for Example 16 using 3-amino-6-bromo-N-(2-methoxyethyl)pyrazine-2-carboxamide. Yield: 44%: $^1$H NMR (DMSO-d$_6$, 400 MHz) δ 11.0 (br s, 1H), 8.98 (s, 1H), 8.92 (s, 1H), 8.46 (d, J=8 Hz, 2H), 7.82 (d, J=8 Hz, 2H), 3.82 (d, J=13 Hz, 2H), 3.50 (s, 3H), 3.45 (d, J=13 Hz, 2H), 3.28 (s, 3H), 3.15 (m, 2H), 2.72 (m, 6H); MS (ES) m/z 435 (M$^+$+1).

Example 19

3-Amino-N-(3-methoxypropyl)-6-{4-[(4-methylpiperazin-1-yl)sulfonyl]phenyl}pyrazine-2-carboxamide hydrochloride Triisopropyl borate (0.82 mL, 3.6 mmol) was added to a stirred solution of 1-[(4-bromophenyl)sulfonyl]-4-methylpiperazine (0.380 g, 1.2 mmol; described: in Keasling, H. H. et rel. *J. Med. Chem.* 1965,8,548-550) in anhydrous tetrahydrofuran (15 mL) at −78° C. under an atmosphere of nitrogen, followed by dropwise addition of n-butyllithium (2.4 mL, 3.6 mmol) over 10 min. The resulting mixture was allowed to warm up to room temperature and was stirred for another 10 min at ambient temperature. HCl (3 M, 1.9 mL, 6.0 mmol) was added and the mixture was stirred for another 10 min, followed by an addition of sodium carbonate (1.26 g, 11.9 mmol). After 30 min, 3-amino-6-bromo-N-(3-methoxypropyl)pyrazine-2-carboxamide (0.24 g, 0.83 mmol) and Pd(dppf)Cl$_2$ (39 mg, 0.05 mmol) were added and the resulting mixture was heated at 65° C. for 22 h. The reaction mixture was evaporated and the residue was dissolved in NaHCO$_3$ (aq. sat.)/ethyl acetate, the aqueous phase was extracted with ethyl acetate and the combined organic phases were evaporated. The crude product was purified on a silica gel column using methylene chloride/methanol/triethyl amine, (9:1:0.1), as the solvent. The product was eluated from the silica with methanol and the solvent was evaporated to give the free base. The base was dissolved in methanol (10 mL) and the mixture was treated with HCl (1.0 M in diethyl ether, 1 mL) followed by addition of diethyl ether (5 mL). The formed precipitate was filtered off and dried at 40° C. in vacuo to give 70 mg (19% yield) of the title compound as a yellow solid: $^1$H NMR (DMSO-d$_6$, 400 MHz) δ 11.02 (br s, 1H), 8.97 (s, 2H), 8.46 (d, J=9 Hz, 2H), 7.82 (d, J=9 Hz, 2H), 3.82 (d, J=13 Hz, 2H), 3.41 (m, 6H), 3.27 (s, 3H), 3.15 (m, 2H), 2.72 (m, 5H), 1.81 (m, 2H); MS (ES) m/z 449 (M$^+$+1).

Example 20

3-Amino-6-{4-[(4-methylpiperazin-1-yl)sulfonyl]phenyl}-N-[3-(2-oxopyrrolidin-1-yl)propyl]pyrazine-2-carboxamide hydrochloride The title compound was prepared as described for Example 19 using 3-amino-6-bromo-N-[3-(2-oxopyrrolidin-1-yl)propyl]pyrazine-2-carboxamide. Yield: 22%: $^1$H NMR (DMSO-d$_6$, 400 MHz) δ; 11.12 (br s, 1H), 9.07 (t, J=6 Hz, 1H), 9.00 (s, 1H), 8.52 (d, J=8 Hz, 2H), 7.80 (d, J=8 Hz, 2H), 3.82 (d, J=12 Hz, 2H), 3.40 (m, 4H), 3.27 (m, 4), 3.16 (m, 2H), 2.73 (m, 5H), 2.25 (t, J=8H, 2H), 1.93 (t, J=7 Hz, 2H), 1.72 (t, J=7 Hz, 2H); MS (ES) m/z 502 (M$^+$+1).

Example 21

3-Amino-N-(cyanomethyl)-6-{4-[(4-methylpiperazin-1-yl)sulfonyl]phenyl}pyrazine-2-carboxamide dihydrochloride The title compound was prepared as described for Example 19 using 3-amino-6-bromo-N-(cyanomethyl)pyrazine-2-carboxamide. Yield: 19%: $^1$H NMR DMSO-d$_6$, 400 MHz) δ 10.49 (br s, 1H), 9.50 (t, J=6 Hz, 1H), 9.05 (s, 1H), 8.49 (d, J=8 Hz, 2H), 7.84 (m, 1H), 7.83 (d, J=81 Hz, 2H), 4.36 (d, J=6 Hz, 2H), 3.83 (d, J=12 Hz, 2H), 3.36 (m, 2H), 3.16 (m, 2H), 2.74 (s, 3H), 2.66 (m, 2H); MS (ES) m/z 416 (M$^+$+1).

Example 22

3-Amino-6-[4-[(4-methyl-1-piperazinyl)sulfonyl]phenyl]-N-[2-(1H-pyrrol-1-yl)ethyl]-2-pyrazinecarboxamide hydrochloride Triethyl amine (0.57 mL, 4.13 mmol) was added to a mixture of 3-amino-6-bromo-2-pyrazinecarboxylic acid (0.30 g, 1.38 mmol; described in: Ellingson, R. C.; Henry, R. L. *J. Am. Chem. Soc.* 1949, 2798-2800), O-(benzotriazol-1-yl)-N,N,N',N'-tetramethyluroniumtetrafluoroborate (0.486 g, 1.51 mmol) and 1-hydroxybenzotriazole (0.204 g, 1.51 mmol) in N,N-dimethylformamide/acetonitrile, (1:1, 5 mL). After stirring for 0.5 h at room temperature, 2-(1H-pyrrol-1-yl)-1-etanamine (0.182 g, 1.65 mmol) was added and the resulting mixture was stirred overnight at room temperature. Approximately, 10 mL water was added and a precipitation was formed. The precipitation was filtered and washed with water which gave 0.21 g (50% yield) of a light brown solid: MS (ESP) m/z 310, 312 (M$^+$+1).

The solid (0.16 g, 0.516 mmol) from previous step was dissolved in tetrahydrofuran/water (5:1, 5 mL) together with [4-[(4-methyl-1-piperazinyl)sulfonyl]phenyl]boronic acid (0.220 g, 0.77 mmol), sodium carbonate (0.164 g, 1.55 mmol) and Pd(dppf)Cl$_2$ (0.013 g, 1.5 mmol). The resulting mixture was stirred at 70° C. overnight (N$_2$-atmosphere). The mixture was evaporated onto silica and purified on silica using toluene/acetonitrile, (1:2 to 1:4), as the eluent which afforded a yellow solid which was dried in vacuo at 40° C. The product was dissolved in a methylene chloride/methanol mixture, (9:1), and hydrochloride acid in diethyl ether (0.28 mL, 1 M) was added. The precipitate was washed with diethyl ether and dried in vacuo to give 69 mg (23% yield) of the title compound: $^1$H NMR (DMSO-d$_6$) δ 8.94 (s, 1H), 8.90 (t, J=6 Hz, 1H), 8.43 (d, J=8 Hz, 2H), 7.82 (d, J=8 Hz, 2H), 6.79 (t, J=2 Hz, 2H), 6.01 (t, J=2 Hz, 2H), 4.12 (t, J=7 Hz, 2H), 3.83 (d, J=12 Hz, 2H), 3.63 (quart, J=6 Hz, 2H), 3.44 (d, J=12 Hz, 2H), 3.15 (m, 2H), 2.73 (m, 5H); $^{13}$C NMR (DMSO-d$_6$) δ 165.8, 154.5, 144.8, 140.8, 135.9, 133.3, 127.9, 126.1, 124.6, 120.7, 107.8, 51.5, 47.6, 43.0, 41.8; MS (ESP) m/z 470 (M$^+$+1).

The following Examples, 23-26, were synthesized as described for Example 22.

Example 23

3-Amino-6-[4-[(4-methyl-1-piperazinyl)sulfonyl] phenyl]-N-[2-(methylsulfonyl)ethyl]-2-pyrazinecarboxamide hydrochloride Starting material: 2-aminoethylmethylsulfone hydrochloride. The title compound was purified by chromatography on silica gel using a gradient toluene/acetonitrile, (1:0 to 1:2), as the eluent, followed by formation of the hydrochloric salt. Yield: 18%: $^1$H NMR (D$_2$O) δ 8.43 (s, 1H), 7.89 (d, J=8 Hz, 2H), 7.74 (d, J=8 Hz, 2H), 3.97 (d, J=14 Hz, 2H), 3.89 (t, J=6 Hz, 2H), 3.63 (m, 4H), 3.29 (m, 2H), 3.25 (s, 3H), 2.94 (s, 3H), 2.88 (t, J=12 Hz, 2H); $^{13}$C NMR (D$_2$O) δ 166.3, 163.3, 143.4, 133.5, 128.4, 125.9, 53.1, 53.0, 43.5, 43.1, 10.9, 33.0; MS (ESP) m/z 483 (M$^+$+1).

Example 24

N-[2-(Acetylamino)ethyl]-3-amino-6-[4-[(4-methyl-1-piperazinyl)sulfonyl]phenyl]-2-pyrazinecarboxamide hydrochloride Starting material: N-acetylethylendiamine. The title compound was purified by chromatography on silica gel using a gradient toluene/acetonitrile, (1:0 to 0:1), as the eluent, followed by formation of the hydrochloric salt. Yield: 25%: $^1$H NMR (D$_2$O) δ 8.42 (s, 1H), 7.93 (d, J=8 Hz, 2H), 7.74 (d, J=8 Hz, 2H), 3.96 (d, J=13 Hz, 2H), 3.64 (d, J=13 Hz, 2H), 3.43 (m, 4H), 3.28 (m, 2H), 2.93 (s, 3H), 2.87 (s, 2H), 2.02 (s, 3H); $^{13}$C NMR (D$_2$O) δ 174.6, 166.1, 152.2, 141.1, 139.9, 136.6, 133.3, 128.2, 125.8, 52.7, 43.3, 42.9, 39.1, 38.7, 22.1; MS (ESP) m/z 462 (M$^+$+1).

Example 25

3-Amino-6-[4-[(4-methyl-1-piperazinyl)sulfonyl] phenyl]-N-[2-(2-oxo-1-imidazolidinyl)ethyl]-2-pyrazinecarboxamide hydrochloride Starting material: 1-(2-aminoethyl)imidazolidin-2-one trifluoroacetic acid (McKay, A. F., Paris, G. Y., Kreling, M.-E. *J. Amer. Chem. Soc.* 1957, 79, 5276). The title compound was purified by chromatography on silica gel using a gradient chloroform/methanol, (98:2 to 4:1), as the eluent, followed by formation of the hydrochloric salt. Yield: 4%: $^1$H NMR (D$_2$O) δ 8.56 (s, 1H), 8.06 (d, J=8 Hz, 2H), 7.83 (d, J=8 Hz, 2H), 3.98 (d, J=14 Hz, 2H), 3.65 (m, 4H), 3.57 (t, J=5 Hz, 2H), 3.45 (m, 4H), 3.28 (m, 2H), 2.93 (s, 3H), 2.86 (m, 2H); MS (ESP) m/z 489 (M$^+$+1).

Example 26

3-Amino-N-[2-(aminosulfonyl)ethyl]-6-[4-[(4-methyl-1-piperazinyl)sulfonyl]phenyl]-2-pyrazinecarboxamide hydrochloride Starting material: 2-aminoethanesulfonic acid amide hydrochloride. The final compound was purified by chromatography on silica gel using a gradient toluene/acetonitrile, (1:0 to 0:1), as the eluent followed by formation of the hydrochloric salt. Yield: 21% of the title is compound as a yellow solid: $^1$H NMR (DMSO-d$_6$) δ 9.13 (t, J=6 Hz, 1H), 8.99 (s, 1H), 8.42 (d, J=8 Hz, 2H), 7.77 (d, J=8 Hz, 2H), 7.03 (s, 2H), 3.74 (quart, J=6 Hz, 2H), 3.28 (m, 2H), 2.95 (br s, 4H), 2.45 (br s, 4H), 2.20 (br s, 3H); MS (ESP) m/z 484(M$^+$+1).

Example 27

Methyl 3-amino-6-[4-(pyrrolidin-1-ylsulfonyl)phenyl]pyrazine-2-carboxylate 4-pyrrolidin-1-ylsulfonyl)phenylboronic acid (0.33 g, 1.29 mmol), methyl 3-amino-6-bromopyrazine-2-carboxylate (0.25 g, 1.08 mmol; described in: H. Ellingson, *J. Amer. Chem. Soc.* 1949, 27.98), K$_3$PO$_3$ (3 M, 1.1 mL, 3.2 mmol), and Pd(dppf)Cl$_2$ (0.044 g, 54 μmol) were suspended in ethylene glycol dimethyl ether/water (1.5:0.5 mL) and heated in a microwave oven at 160° C. for 10 min. The reaction was repeated 3 times. The combined product mixtures were evaporated with silica gel and the crude product was purified by chromatography on silica gel using a heptan/ethylacetate gradient as the eluent to give 0.96 g (82% yield) of the title compound: MS (ES) m/z 363 (M$^+$+1).

Example 28

Methyl 3-{[2,6-dimethoxy-4-(2-phenylethoxy)benzyl]amino}-6-[4-(pyrrolidin-1-ylsulfonyl)phenyl] pyrazine-2-carboxylate polystyrene Sodiumtriacetoxy borohydride (2.6 g, 12.2 mmol) in N,N-dimethylformamide/acetic acid, (98:2, 20 mL), and trimethylsilyl chloride (1.17 mL, 9.18 mmol) was added to a mixture of methyl 3-amino-6-[4-(pyrrolidin-1-ylsulfonyl)phenyl) pyrazine-2-carboxylate (4.4 g, 12.2 mmol) and 2-(3,5-dimethoxy-4-formylphenoxy) ethyl polystyrene (12 g, 0.51 mmol/g) in N,N-dimethylformamide (60 mL). The mixture was shaken for 3 h and then filtered. The polystyrene resin was washed, three times, with N,N-dimethylformamide and three times with methylene chloride. The procedure was repeated using sodiumtriacetoxy borohydride (2.6 g, 12.24 mmol) in N,N-dimethylformamide/acetic acid (98:2, 20 mL), trimethylsilyl chloride (1.17 ml, 9.18 mmol) and methyl 3-amino-6-[4-(pyrrolidin-1-ylsulfonyl)phenyl]pyrazine-2-carboxylate (12 g, 0.51 mmol/g) and shaking was continued for 18 h. The polystyrene resin was washed, three times, with N,N-dimethylformamide, three times with methylene chloride and three times with methanol. The resin was dried under vacuum to give 12.5 g of the title compound.

Analysis: The title compound (50 mg) was treated with trifluoroacetic acid in methylene is chloride (conc. 95%) for 30 min, filtered and the solvent was analyzed by MS: MS (ESI) 363 m/z ($M^++1$) (which corresponds to the starting material).

Example 29

3-{[2,6-Dimethoxy-4-(2-phenylethoxy)benzyl]amino}-6-[4-(pyrrolidin-1-ylsulfonyl)phenyl]pyrazine-2-carboxylic acid polystyrene An aqueous solution of lithium hydroxide (4 M, 10 mL) was added to a suspension of methyl 3-{[2,6-dimethoxy-4-(2-phenylethoxy)benzyl]amino}-6-[4-(pyrrolidin-1-ylsulfonyl)phenyl]pyrazine-2-carboxylate polystyrene (12 g, 0.51 mmol/g) in tetrahydrofuran (100 mL). The mixture was shaken for 17 h. Filtering and washing of the resin three times with N,N-dimethylformamide/water, (4:1), and three times with N,N-dimethylformamide/acetic acid, (98:2), and three times with methanol and drying of the resin gave 11.8 g of the title compound.

Analysis: The title compound (50 mg) was treated with trifluoroacetic acid in methylene chloride (conc. 95%) for 30 min, filtered and the solvent was analyzed by MS: MS (ESI) 349 m/z ($M^++1$).

Example 30

3-Amino-N-(2-cyanoethyl)-6-(4-(pyrrolidin-1-ylsulfonyl)phenyl]pyrazine-2-carboxamide 3-Aminopropanenitrile (36 mg, 0.51 mmol), O-(benzotriazol-1-yl)-N,N,N',N'-tetramethyluronium tetrafluoroborate (0.164 g, 0.51 mmol) and 1-hydroxybenzotriazole hydrate (69 mg, 0.51 mmol) was added to 3-{[2,6-dimethoxy-4-(2-phenylethoxy)benzyl]amino}-6-[4-(pyrrolidin-1-ylsulfonyl)phenyl]pyrazine-2-carboxylic acid polystyrene (0.50 g, 0.51 mmol/g, 0.255 mmol) in N,N-dimethylformamide (2 mL). The mixture was shaken for 5 min where after diisopropylethyl amine (0.133 mL, 0.765 mmol) was added. The mixture was shaken for 18 h, filtered and washed with N,N-dimethylformamide and three times with methylene chloride. The product was isolated by treating the resin with trifluoroacetic acid in methylene chloride (conc. 95%) for 30 min and then filtered. The solution was evaporated and purification by preparative HPLC (column: XTerra C8 19×300 mm, eluent: gradient acetonitrile/water, (20:80 to 80:20)), gave 1 mg (1% yield) of the title compound: $^1$H NMR (CDCl$_3$, 400 MHz) δ 8.70 (s, 1H), 8.01 (d, J=8 Hz, 2H), 7.93 (d, J=8 Hz, 2H), 3.79 (m, 2H), 3.30 (m, 4H), 2.79 (t, J=6 Hz, 2H), 1.80 (m, 4H); MS (ESI) 401 m/z ($M^++1$).

The following Examples, 31-35, were synthesized as described for Example 30.

Example 31

3-Amino-N-(3-amino-3-oxopropyl)-6-[4-(pyrrolidin-1-ylsulfonyl)phenyl]pyrazine-2-carboxamide Starting material: β-alaninamide. Yield: 2%: $^1$H NMR (CDCl$_3$, 400 MHz) δ 8.60 (s, 1H), 8.03 (d, J=8 Hz, 2H), 7.85 (d, J=8 Hz, 2H), 3.64 (t, J=6 Hz, 2 M, 3.20 (m, 4H), 2.50 (t, J=6 Hz, 2H), 1.72 (m, 4H); MS (ESI) 419 m/z ($M^++1$).

Example 32

3-Amino-N-(2-nitrobenzyl)-6-[4-(pyrrolidin-1-ylsulfonyl)phenyl]pyrazine-2-carboxamide Starting material: 1-(2-nitrophenyl)methanamine. Yield: 1.8%: $^1$H NMR (CDCl$_3$, 400 MHz) δ 8.80 (s, H), 8.70 (s, H), 8.12 (d, J=7 Hz, 1H), 8.04 (d, J=8 Hz, 2H), 7.90 (d, J=8 Hz, 2H), 7.73 (dd, J=8 Hz, 1H), 7.50 (m, 1H), 7.66 (m, 1H), 4.94 (d, J=7 Hz, 2H), 3.30 (m, 4H), 1.8 (m, 4H); MS (ESI) 483 m/z ($M^++1$).

Example 33

3-Amino-N-(2-methoxybenzyl)-6-[4-(pyrrolidin-1-ylsulfonyl)phenyl]pyrazine-2-carboxamide Starling material: 1-(2-methoxyphenyl)methanamine. Yield: 1.6%: $^1$H NMR (CDCl$_3$, 400 MHz) δ 8.64 (s, 1H), 8.01 (d, J=8 Hz, 2H), 7.89 (d, J=8 Hz, 2H), 7.31 (d, J=7 Hz, 2H), 6.94 (m, 2H), 4.68 (d, J=6 Hz, 2H), 3.94 (m, 3H), 3.41 (m, 1H), 3.27 (m, 4H), 1.8 (m, 4H); MS (ESI) 468 m/z ($M^++1$).

Example 34

3-Amino-N-(3-morpholin-4-ylpropyl)-6-[4-(pyrrolidin-1-ylsulfonyl)phenyl]pyrazine-2-carboxamide Starting material: 3-morpholin-4-ylpropan-1-amine. Yield: 1.4%: $^1$H NMR (CDCl$_3$, 400 MHz) δ 8.67 (s, 1H), 8.02 (d, J=8 Hz, 2H), 7.94 (d, J=8 Hz, 2H), 3.66 (t, J=5 Hz, 4H), 3.58 (m, 2H), 3.30 (m, 4H), 2.49 (t, J=7 Hz, 2H), 2.48 (m, 4H), 1.85 (t, J=7 Hz, 2H), 1.79 (m, 4H); MS (ESI) 475 m/z ($M^++1$).

Example 35

3-Amino-N-[3-(4-methylpiperazin-1-yl)propyl]-6-[4-(pyrrolidin-1-ylsulfonyl)phenyl]pyrazine-2-carboxamide Starting material: 3-(4-methylpiperazin-1-yl)propan-1-amine. Yield: 3.8%: $^1$H NMR (CD$_3$OD, 400 MHz) δ 8.77 (s, 1H), 8.24 (d, J=8 Hz, 2H), 7.05 (d, J=8 Hz, 2H), 3.54 (t, J=7 Hz, 2H), 3.36 (m, 4H), 3.32 (m, 4H), 2.56 (d, J=7 Hz, 4H), 2.28 (s, 3H), 2.09 (s, 1H), 1.90 (m, 2H), 1.84 (m, 4H); MS (ESI) 488 m/z ($M^++1$).

Pharmaceutical Compositions

According to one aspect of the present invention there is provided a pharmaceutical composition comprising a compound of formula I, as a free base or a pharmaceutically acceptable salt, solvate or solvate of salt thereof, for use in the prevention and/or treatment of conditions associated with glycogen synthase kinase-3.

The composition may be in a form suitable for oral administration, for example as a tablet, for parenteral injection as a sterile solution or suspension. In general the above compositions may be prepared in a conventional manner using pharmaceutically carriers or diluents. Suitable daily doses of the compounds of formula I in the treatment of a mammal, including man, are approximately 0.01 to 250 mg/kg bodyweight at peroral administration and about 0.001 to 250 mg/kg bodyweight at parenteral administration. The typical daily dose of the active ingredients varies within a wide range and will depend on various factors such as the relevant indication, the route of administration, the age, weight and sex of the patient and may be determined by a physician.

A compound of formula I, or a pharmaceutically acceptable salt, solvate or solvate of salt thereof, can be used on its own but will usually be administered in the form of a pharmaceutical composition in which the formula I compound/salt/solvate (active ingredient) is in association with a pharmaceutically acceptable diluent or carrier. Dependent on the mode of administration, the pharmaceutical composition may comprise from 0.05 to 99% w (percent by weight), for example from 0.10 to 50% w, of active ingredient, all percentages by weight being based on total composition.

A diluent or carrier includes water, aqueous polyethylene glycol, magnesium carbonate, magnesium stearate, talc, a sugar (such as lactose), pectin, dextrin, starch, tragacanth, microcrystalline cellulose, methyl cellulose, sodium carboxymethyl cellulose or cocoa butter.

A composition of the invention can be in tablet or injectable form. The tablet may additionally comprise a disintegrant and/or may be coated (for example with an enteric coating or coated with a coating agent such as hydroxypropyl methylcellulose).

The invention further provides a process for the preparation of a pharmaceutical composition of the invention which comprises mixing a compound of formula I, or a pharmaceutically acceptable salt, solvate or solvate of salt thereof, a hereinbefore defined, with a pharmaceutically acceptable diluent or carrier.

An example of a pharmaceutical composition of the invention is an injectable solution containing a compound of the invention, or a a pharmaceutically acceptable salt, solvate or solvate of salt thereof, as hereinbefore defined, and sterile water, and, if necessary, either sodium hydroxide or hydrochloric acid to bring the pH of the final composition to about pH 5, and optionally a surfactant to aid dissolution.

Liquid solution comprising a compound of formula I, as a free base or a pharmaceutically acceptable salt, solvate or solvate of a salt thereof, dissolved in water.

| Solution | mg/mL |
| --- | --- |
| Compound X | 5.0% w/v |
| Pure water | To 100% |

Medical Use

Surprisingly, it has been found that the compounds defined in the present invention, as a free base or a pharmaceutically acceptable salt, solvate or solvate of salt thereof, are well suited for inhibiting glycogen synthase kinase-3 (GSK3). Accordingly, the compounds of the present invention are expected to be useful in the prevention and/or treatment of conditions associated with glycogen synthase kinase-3 activity, i.e. the compounds may be used to produce an inhibitory effect of GSK3 in mammals, including man, in need of such prevention and/or treatment.

GSK3 is highly expressed in the central and peripheral nervous system and in other tissues. Thus, it is expected that compounds of the invention are well suited for the prevention and/or treatment of conditions associated with glycogen synthase kinase-3 in the central and peripheral nervous system. In particular, the compounds of the invention are expected to be suitable for prevention and/or treatment of conditions associated with especially, dementia, Alzheimer's Disease, Parkinson's Disease, Frontotemporal dementia Parkinson's Type, Parkinson dementia complex of Guam, HIV dementia, diseases with associated neurofibrillar tangle pathologies and dementia pugilistica.

Other conditions are selected from the group consisting of amyotrophic lateral sclerosis, corticobasal degeneration, Down syndrome, Huntington's Disease, postencephelatic parkinsonism, progressive supranuclear palsy, Pick's Disease, Niemann-Pick's Disease, stroke, head trauma and other chronic neurodegenerative diseases, Bipolar Disease, affective disorders, depression, schizophrenia, cognitive disorders, hair loss and contraceptive medication, Type I and Type II diabetes, diabetic neuropathy and diabetes related disorders.

Further conditions are selected from the group consisting predemented states, Mild Cognitive Impairment, Age-Associated Memory Impairment, Age-Related Cognitive Decline, Cognitive Impairement No Dementia, mild cognitive decline, mild neurocognitive decline, Late-Life Forgetfulness, memory impairment and cognitive impairment, vascular dementia, dementia with Lewy bodies and androgenetic alopecia.

One embodiment of the invention relates to the prevention and/or treatment of dementia and Alzheimer's Disease.

Another embodiment of the invention relates to the prevention and/or treatment of Type I and Type II diabetes, diabetic neuropathy and diabetes related disorders.

The dose required for the therapeutic or preventive treatment of a particular disease will necessarily be varied depending on the host treated, the route of administration and the severity of the illness being treated.

The present invention relates also to the use of a compound of formula I as defined hereinbefore, in the manufacture of a medicament for the prevention and/or treatment of conditions associated with glycogen synthase kinase-3.

In the context of the present specification, the term "therapy" also includes "prevention" unless there are specific indications to the contrary. The terms "therapeutic" and "therapeutically" should be construed accordingly.

The invention also provides for a method of treatment and/or prevention of conditions associated with glycogen synthase kinase-3 comprising administrering to a mammal, including man in need of such treatment and/or prevention a therapeutically effective amount of a compound of formula I, as hereinbefore defined.

Non-Medical Use

In addition to their use in therapeutic medicine, the compounds of formula I as a free base or a pharmaceutically acceptable salt, solvate or solvate of a salt thereof, are also useful as pharmacological tools in the development and standardisation of in vitro and in vivo test systems for the evaluation of the effects of inhibitors of GSK3 related activity in laboratory animals such as cats, dogs, rabbits, monkeys, rats and mice, as part of the search for new therapeutics agents.

Pharmacology

Determination of ATP Competition in Scintillation Proximity GSK3β Assay.

GSK3β Scintillation Proximity Assay.

The competition experiments were carried out in duplicate with 10 different concentrations of the inhibitors in clear-bottom microtiter plates (Wallac, Finland). A biotinylated peptide substrate, Biotin-Ala-Ala-Glu-Glu-Leu-Asp-Ser-Arg-Ala-Gly-Ser($PO_3H_2$)-Pro-Gln-Leu (AstraZeneca, Lund), was added at a final concentration of 1 μM in an assay buffer containing 1 mU recombinant human GSK3β (Dundee University, UK), 12 mM morpholinepropanesulfonic acid (MOPS), pH 7.0, 0.3 mM EDTA, 0.01% β-mercaptoethanol, 0.004% Brij 35 (a natural detergent), 0.5% glycerol and 0.5 μg BSA/25 μl. The reaction was initiated by the addition of 0.04 μCi [γ-$^{33}$P]ATP (Amersham, UK) and unlabelled ATP at a final concentration of 1 μM and assay volume of 25 μl. After incubation for 20 minutes at room temperature, each reaction was terminated by the addition of 25 μl stop solution containing 5 mM EDTA, 50 μM ATP, 0.1% Triton X-100 and 0.25 mg streptavidin coated Scintillation Proximity Assay (SPA) beads (Amersham, UK). After 6 hours the radioactivity was determined in a liquid scintillation counter (1450 MicroBeta Trilux, Wallac). The inhibition curves were analysed by non-linear regression using GraphPad Prism, USA. The $K_m$ value of ATP for GSK3β, used to calculate the inhibition constants ($K_i$) of the various compounds, was 20 μM.

The following abbreviations have been used:

| | |
|---|---|
| MOPS | Morpholinepropanesulfonic acid |
| EDTA | Ethylenediaminetetraacetic acid |
| BSA | Bovin Serum Albumin |
| ATP | Adenosine Triphosphate |
| SPA | Scintillation Proximity Assay |
| GSK3 | Glycogen synthase kinase 3 |

Results

Typical $K_i$ values for the compounds of the present invention are in the range of about 0.001 to about 10,000 nM. Other values for $K_i$ are in the range of about 0.001 to about 1000 nM. Further values for $K_i$ are in the range of about 0.001 nM to about 300 nM.

The invention claimed is:
1. A compound of the following formula

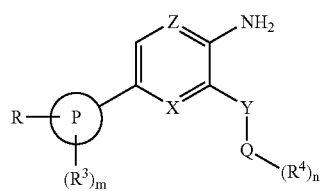

(I)

wherein:
Z is N;
Y is $CONR^5$, $NR^5CO$, $SO_2NR^5$, $NR^5SO_2$, $CH_2NR^5$, $NR^5CONR^5$, $CH_2CO$, $CO$ or $CH_2O$;
X is N;
P is phenyl;
Q is $C_{1-6}$alkyl;
R is $C_{0-6}$alkyl$(SO_2)NR^1R^2$;
$R^1$ and $R^2$ together form a 1-pyrrolidinyl or 1-piperazinyl moiety, wherein said 1-pyrrolidinyl or 1-piperazinyl moiety may be optionally substituted by A;
$R^4$ is independently selected from CN, $OR^6$, $CONR^6R^7$, $NR^6COR^7$, $(SO)NR^6R^7$, $SO_2R^6$, phenyl, 1-imidazolyl, 1-imidazolidinyl, 4-morpholinyl, 1-oxopyrrolidinyl, 1-piperazinyl, 1-pyrrolinyl, 2-thienyl moiety, wherein said phenyl ring or 1-imidazolyl, 1-imidazolidinyl, 4-morpholinyl, 1-oxopyrrolidinyl, 1-piperazinyl, 1-pyrrolinyl, 2-thienyl moiety may be optionally be substituted with A;
n is 1;
$R^5$ is hydrogen or $C_{1-6}$alkyl;
$R^6$ and $R^7$ are independently selected from hydrogen, or $C_{1-6}$alkyl
A is oxo (=O), nitro, $OR^6$ or $C_{1-6}$alkyl;
as a free base or a pharmaceutically acceptable thereof.

2. A compound according to claim 1, wherein said $R^4$ is 1-piperazinyl optionally substituted by A, which A is a $C_{1-6}$alkyl.

3. A compound according to any one of claims 1 or 2, wherein Y is $CONR^5$; and $R^5$ is hydrogen.

4. A compound according to claim 1 which is
3-Amino-N-(2-cyanoethyl)-6-[4-(pyrrolidin-1-ylsulfonyl)phenyl]pyrazine-2-carboxamide;
3-Amino-N-(3-amino-3-oxopropyl)-6-[4-(pyrrolidin-1-ylsulfonyl)phenyl]pyrazine-2-carboxamide;
3-Amino-N-(2-nitrobenzyl)-6-[4-(pyrrolidin-1-ylsulfonyl)phenyl]pyrazine-2-carboxamide;
3-Amino-N-(2-methoxybenzyl)-6-[4-(pyrrolidin-1-ylsulfonyl)phenyl]pyrazine-2-carboxamide;
3-Amino-N-(3-morpholin-4-ylpropyl)-6-[4-(pyrrolidin-1-ylsulfonyl)phenyl]pyrazine-2-carboxamide, or
3-Amino-N-[3-(4-methylpiperazin-1-yl)propyl]-6-[4-(pyrrolidin-1-ylsulfonyl)phenyl]pyrazine-2-carboxamide;
as a free base or a pharmaceutically acceptable salt, thereof.

5. A compound according to claim 1 which is
3-Amino-N-(2-morpholin-4-ylethyl)-6-[4-(pyrrolidin-1-ylsulfonyl)phenyl]pyrazine-2-carboxamide hydrochloride;
3-Amino-N-[2-(1H-imidazol-4-yl)ethyl]-6-[4-(pyrrolidin-1-ylsulfonyl)phenyl]pyrazine-2-carboxamide hydrochloride;
3-Amino-N-[3-(1H-imidazol-1-yl)propyl]-6-[4-(pyrrolidin-1-ylsulfonyl)phenyl]pyrazine-2-carboxamide hydrochloride;
3-Amino-6-{4-[(4-methylpiperazin-1-yl)sulfonyl]phenyl}-N-(2-thien-2-ylethyl)pyrazine-2-carboxamide hydrochloride;
3-Amino-6-{4-[(4-methylpiperazin-1-yl)sulfonyl]phenyl}-N-(thien-2-ylmethyl)pyrazine-2-carboxamide hydrochloride;
3-Amino-N-(2-methoxyethyl)-6-{4-[(4-methylpiperazin-1-yl)sulfonyl]phenyl}pyrazine-2-carboxamide hydrochloride;
3-Amino-N-(3-methoxypropyl)-6-{4-[(4-methylpiperazin-1-yl)sulfonyl]phenyl}pyrazine-2-carboxamide hydrochloride;
3-Amino-6-{4-[(4-methylpiperazin-1-yl)sulfonyl]phenyl}-N-[3-(2-oxopyrrolidin-1-yl)propyl]pyrazine-2-carboxamide hydrochloride;
3-Amino-N-(cyanomethyl)-6-{4-[(4-methylpiperazin-1-yl)sulfonyl]phenyl}pyrazine-2-carboxamide dihydrochloride;

3-Amino-6-[4-[(4-methyl-1-piperazinyl)sulfonyl]phenyl]-N-[2-(1H-pyrrol-1-yl)ethyl]-2-pyrazinecarboxamide hydrochloride;

3-Amino-6-[4-[(4-methyl-1-piperazinyl)sulfonyl]phenyl]-N-[2-(methylsulfonyl)ethyl]-2-pyrazinecarboxamide hydrochloride;

N-[2-(Acetylamino)ethyl]-3-amino-6-[4-[(4-methyl-1-piperazinyl)sulfonyl]phenyl]-2-pyrazinecarboxamide hydrochloride;

3-Amino-6-[4-[(4-methyl-1-piperazinyl)sulfonyl]phenyl]-N-[2-(2-oxo-1-imidazolidinyl)ethyl]-2-pyrazinecarboxamide hydrochloride;

3-Amino-N-[2-(aminosulfonyl)ethyl]-6-[4-[(4-methyl-1-piperazinyl)sulfonyl]phenyl]-2-pyrazinecarboxamide hydrochloride;

or a free base of any said hydrochloride or a pharmaceutically acceptable salt of any said free base.

6. A pharmaceutical formulation comprising as active ingredient a therapeutically effective amount of a compound according to claim 3 in association with a pharmaceutically acceptable carrier or diluent.

7. A pharmaceutical formulation comprising as active ingredient a therapeutically effective amount of a compound according to any one of claims 1, 2, 4 or 5 in association with a pharmaceutically acceptable carrier or diluent.

\* \* \* \* \*

UNITED STATES PATENT AND TRADEMARK OFFICE
CERTIFICATE OF CORRECTION

PATENT NO. : 7,595,321 B2
APPLICATION NO. : 10/539545
DATED : September 29, 2009
INVENTOR(S) : Berg et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 949 days.

Signed and Sealed this

Twenty-eighth Day of September, 2010

David J. Kappos
*Director of the United States Patent and Trademark Office*